(12) United States Patent
Freitag et al.

(10) Patent No.: US 6,410,341 B1
(45) Date of Patent: *Jun. 25, 2002

(54) ANALYTICAL TEST DEVICE AND METHOD FOR USE IN MEDICAL DIAGNOSES

(75) Inventors: Helmut E. Freitag, Birmingham (GB); Qinwei Shi, Etobicoke (CA); Charles A. Harrington, Austin, TX (US)

(73) Assignee: Spectral Diagnostics, Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/353,188

(22) Filed: Jul. 14, 1999

Related U.S. Application Data

(63) Continuation-in-part of application No. 09/130,164, filed on Aug. 6, 1998.

(51) Int. Cl.⁷ .............................................. G01N 33/558
(52) U.S. Cl. ..................... 436/514; 436/516; 436/518; 436/164; 436/165; 436/69; 436/811; 436/815; 435/5; 435/7.1; 435/7.2; 435/7.24; 435/7.29; 435/7.92; 435/6; 435/91.2; 435/287.2; 435/288.2; 422/56; 422/57; 422/58; 422/61; 422/72; 422/82.06
(58) Field of Search .............................. 435/5, 7.1, 7.2, 435/7.24, 7.29, 7.92, 287.2, 288.2, 6, 91.2; 436/514, 516, 518, 164, 165, 69, 811, 815; 422/56, 57, 58, 61, 72, 82.06

(56) References Cited

U.S. PATENT DOCUMENTS

| 4,477,575 A | 10/1984 | Vogel et al. |
| 4,753,776 A | 6/1988 | Hillman et al. |
| 4,774,192 A | 9/1988 | Terminiello et al. |
| 4,861,711 A | 8/1989 | Friesen et al. |
| 4,933,092 A | 6/1990 | Aunet et al. |
| 4,987,065 A | 1/1991 | Stavrianopoulos et al. |
| 5,075,078 A | 12/1991 | Osikowicz et al. |
| 5,079,142 A | 1/1992 | Coleman et al. |
| 5,096,809 A | 3/1992 | Chen et al. |
| 5,110,724 A | 5/1992 | Hewett |
| 5,120,643 A | 6/1992 | Ching et al. |
| 5,135,716 A | 8/1992 | Thakore |
| 5,141,850 A | 8/1992 | Cole et al. |
| 5,144,890 A | 9/1992 | Korhonen |
| 5,290,678 A | 3/1994 | Jackowski |
| 5,413,732 A | 5/1995 | Buhl et al. |
| 5,591,645 A | 1/1997 | Rosenstein |
| 5,747,274 A | * 5/1998 | Jackowski .................. 435/7.94 |
| 5,885,526 A | * 3/1999 | Chu et al. ...................... 422/56 |
| 5,939,331 A | * 8/1999 | Burd et al. .................. 436/518 |
| 5,985,675 A | * 11/1999 | Charm et al. ................ 436/514 |

OTHER PUBLICATIONS

Galpre and Milstein et al., 1977, Nature, 266:550–2.

* cited by examiner

Primary Examiner—Christopher L. Chin
Assistant Examiner—Minh-Quan K. Pham
(74) Attorney, Agent, or Firm—Klauber & Jackson

(57) ABSTRACT

An analytical test device is described for the immunochromatographic determination of the presence of one or more analytes in fluid samples. The device is configured such that the sample is allowed to enter the detection zone simultaneously from many different directions, eliminating stagnation of the flow of the sample. By selection of the porous substrate, the device also allows for the separation of red blood cells from plasma, providing a rapid test for one or more analytes in a sample of whole blood. The device of the present invention may measure more than one analyte simultaneously from a single sample, either by having multiple immunochromatographic pathways fed by a single sample, or multiple analytes detected in the same pathway by way of multiple capture antibodies.

64 Claims, 10 Drawing Sheets

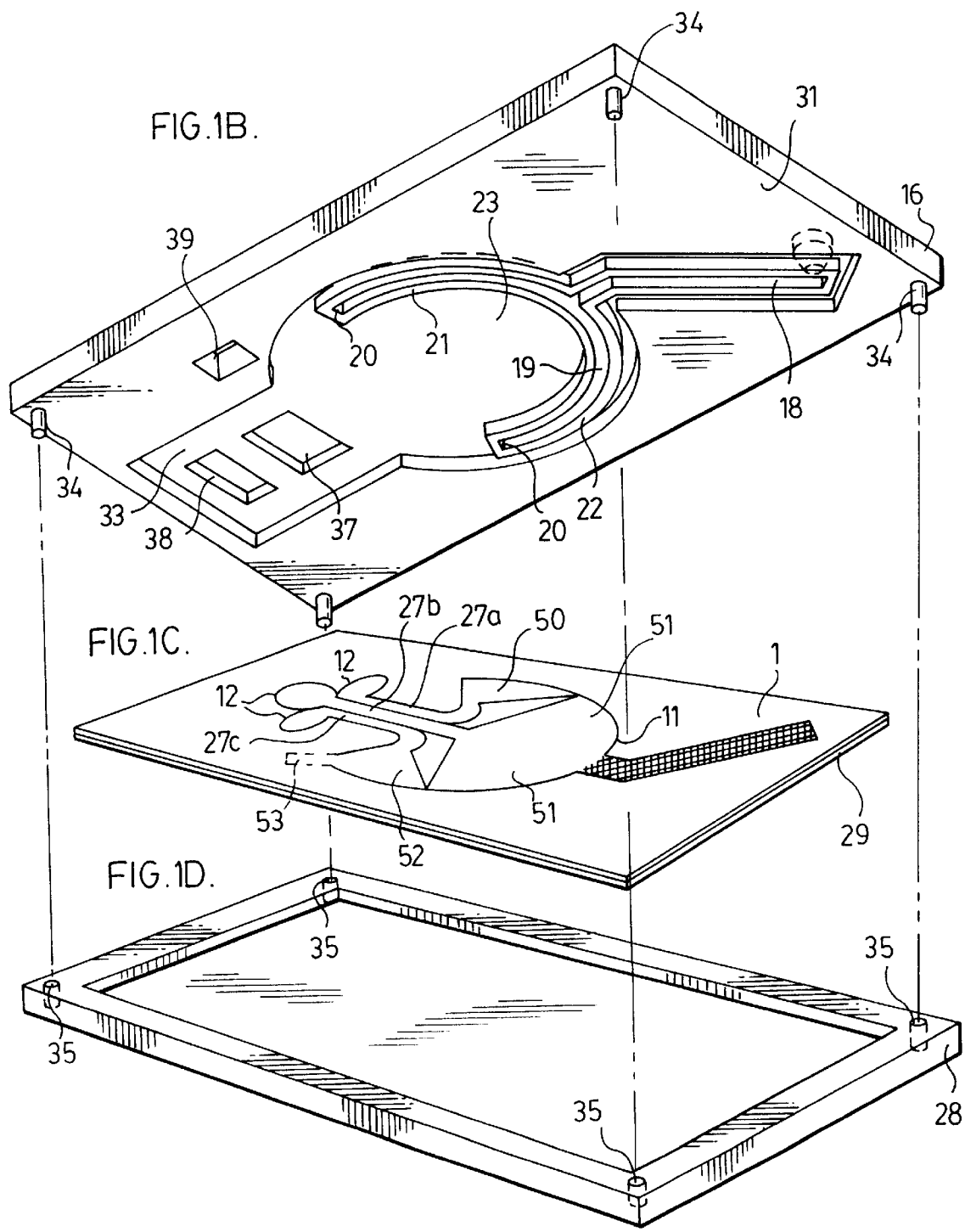

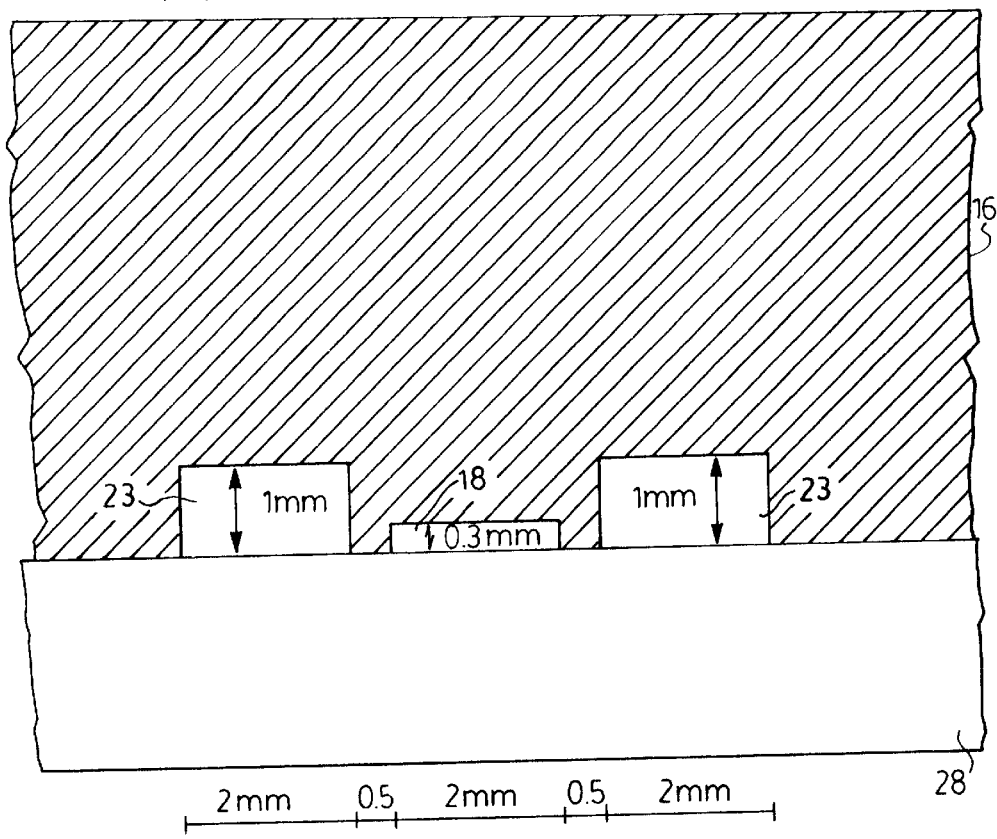
FIG.4. A-A
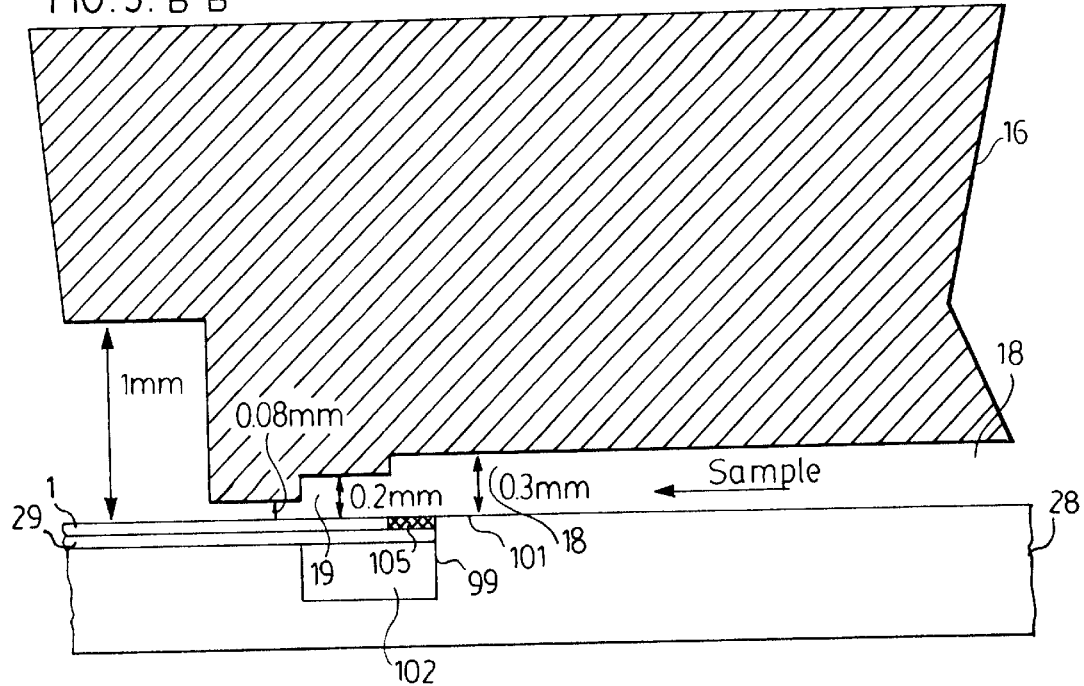
FIG.5. B-B

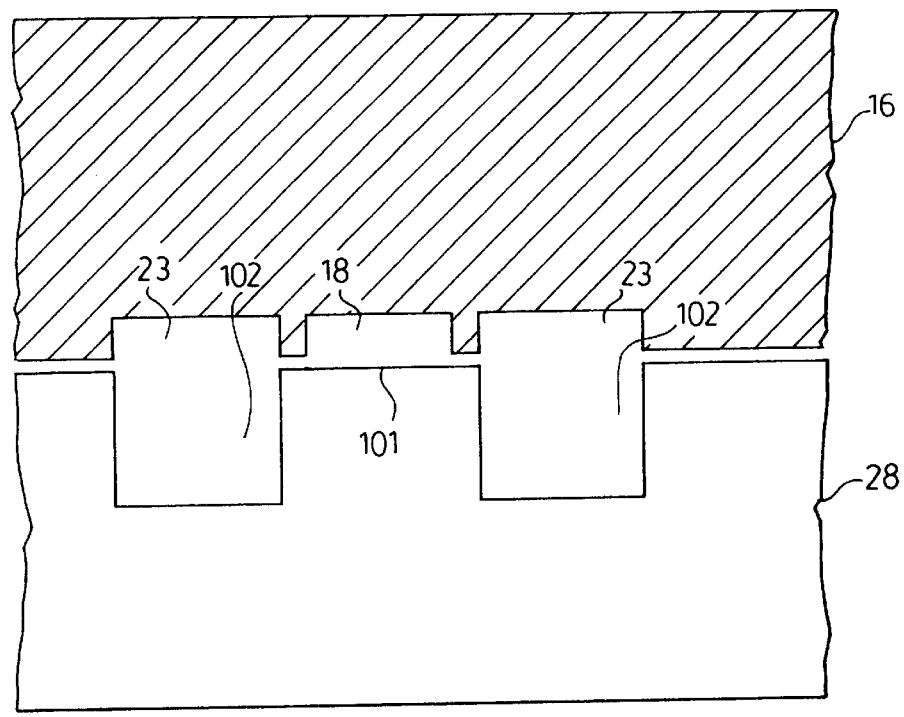
FIG. 6. C-C
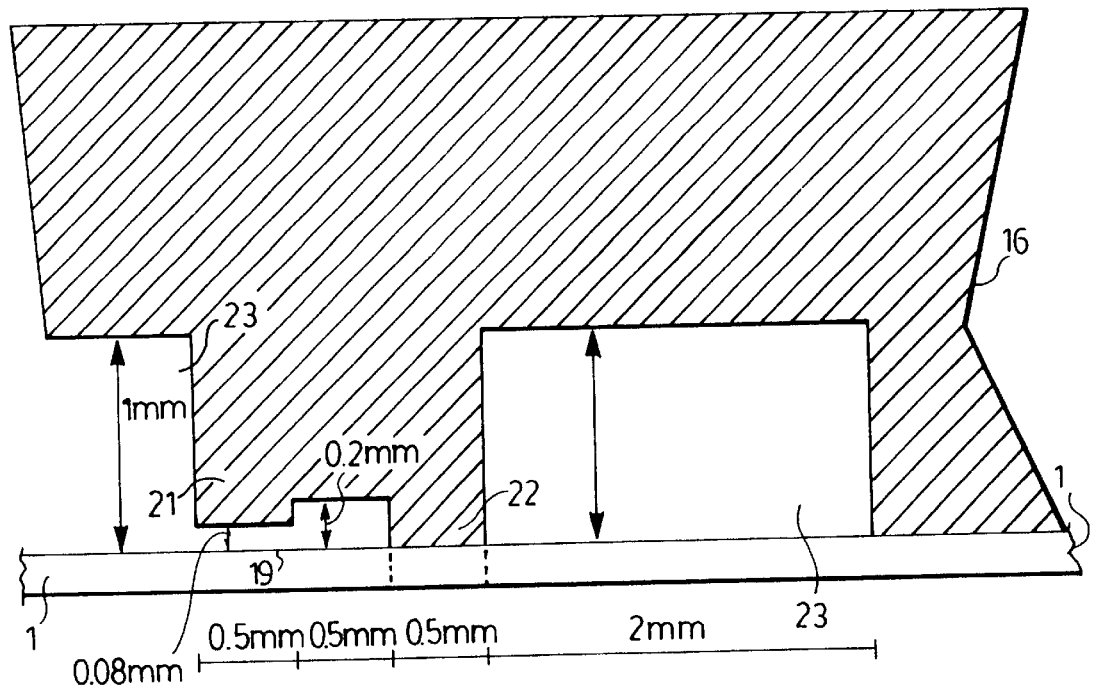
FIG. 7. D-D

FIG.12A
FIG.12B.
E-E
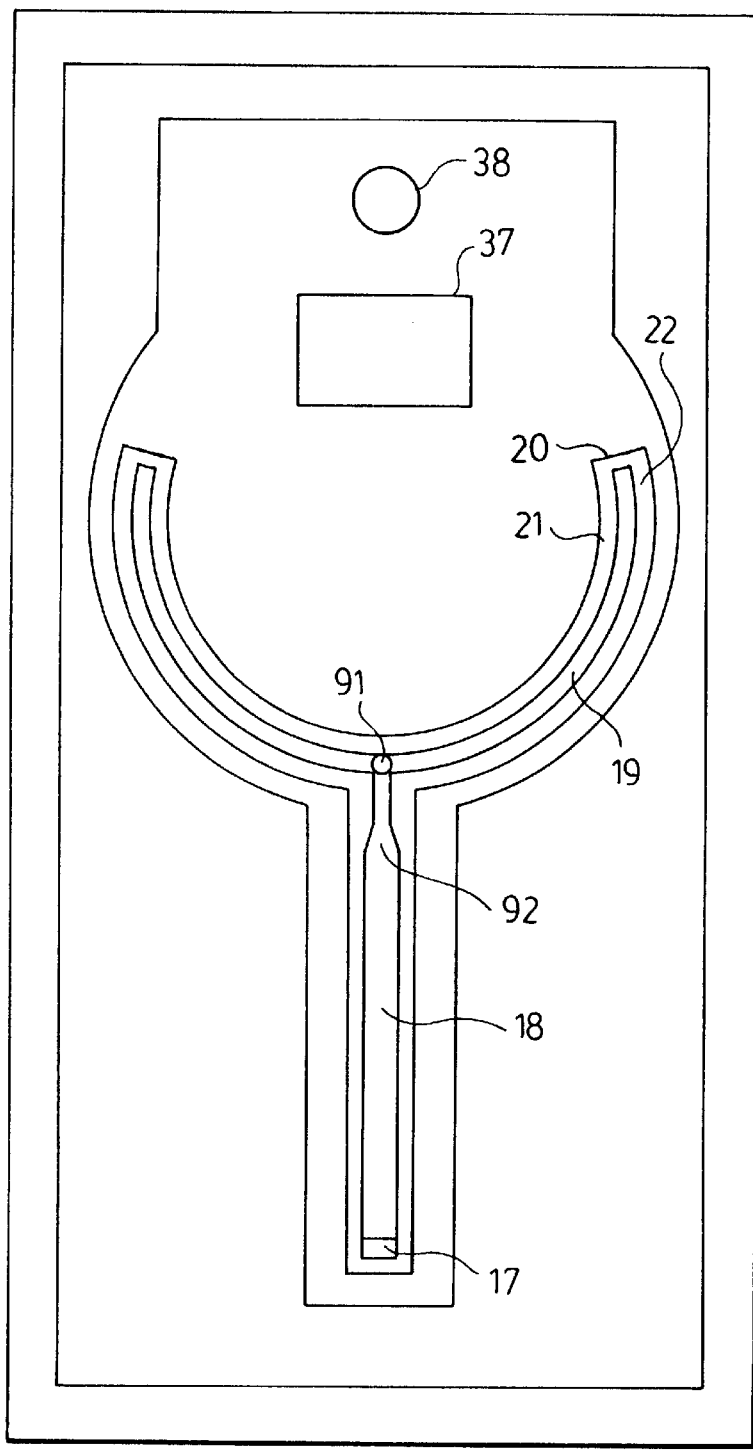
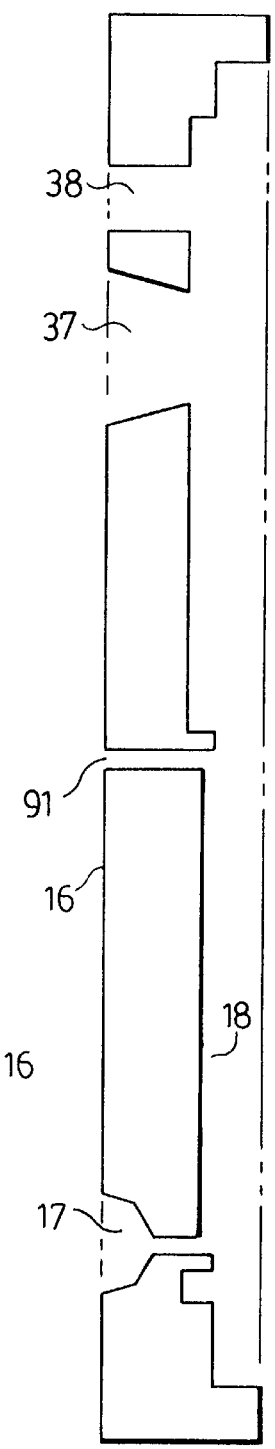

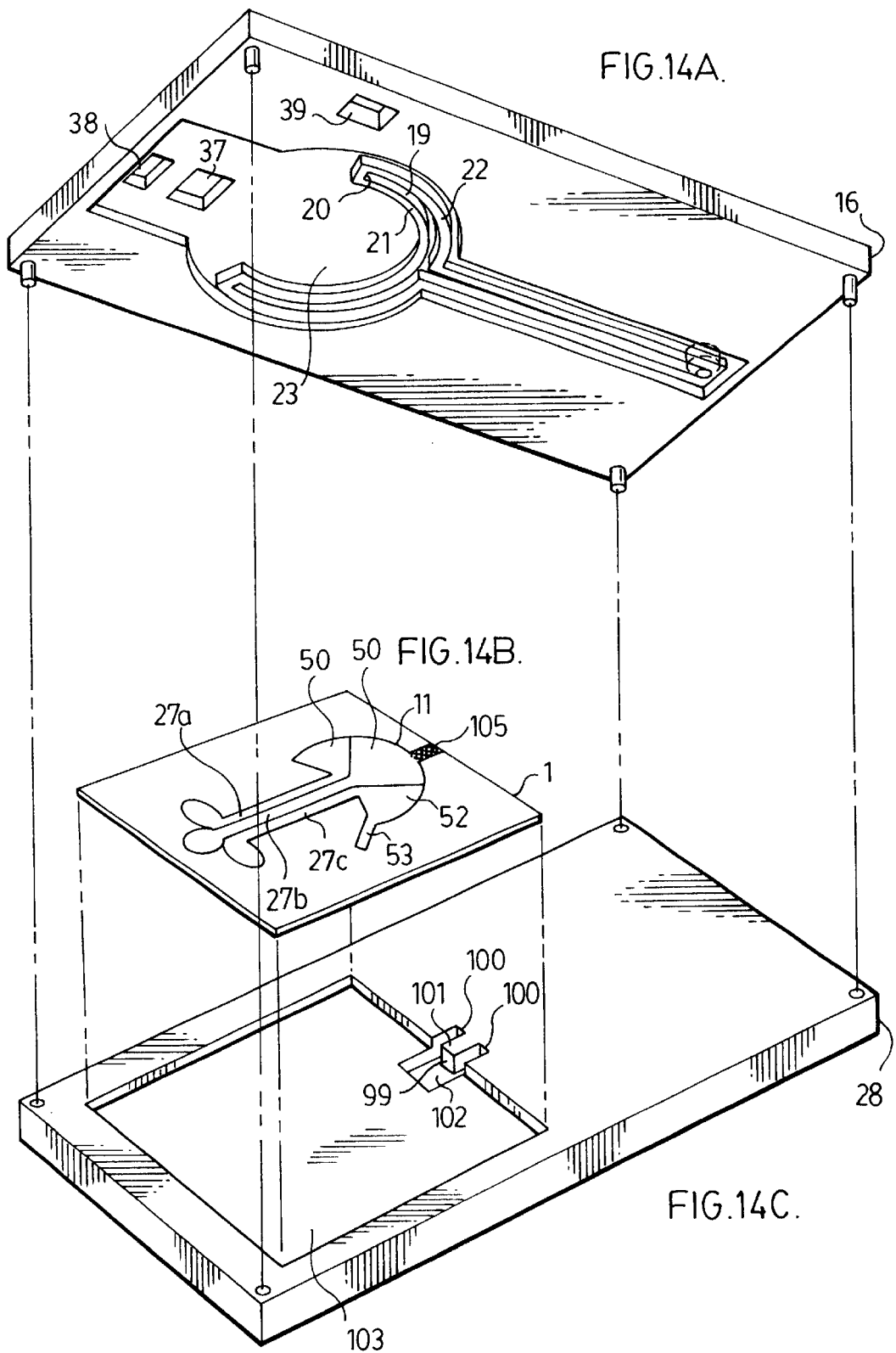

ANALYTICAL TEST DEVICE AND METHOD FOR USE IN MEDICAL DIAGNOSES

CROSS-REFERENCED RELATED APPLICATIONS

This application is a Continuation-In-Part of Ser. No. 09/130,164, filed Aug. 6, 1998, incorporated herein by reference in its entirety.

FIELD OF THE INVENTION

This invention relates to analytical test devices and methods useful for analytical assays to determine the presence of analytes in fluid samples. It is especially useful for determining the presence of cardiac analytes in whole blood, although it is not so limited.

BACKGROUND OF THE INVENTION

The product and procedures of this invention can be utilized for many diagnostic purposes as well as for following the course of mammalian diseases and therapeutic treatments. It is applicable to many mammalian body fluids such as whole blood, serum, plasma and urine. Although this invention will be principally discussed as applied to detecting cardiac analytes it may also be applicable to other fields where antigen/antibody or equivalent reactions are utilized.

Many related assay procedures especially those including immunoassays may be performed using the device of the present invention and its disclosed modifications. For example, immunoassays or non-immunoassay test formats employing separation of red blood cells from plasma and a lateral fluid path may be employed. Analytes such as hormones for determining pregnancy or ovulation; viral, bacterial and fungal infectious microorganisms including *H. pylori* for gastrointestinal ulcers, drugs of use and abuse and tumor markers are non-limiting examples. Enzymatic assays such as those which determine levels of glucose and other analytes in blood by formation of a chromogen are also contemplated by the present invention.

A number of immunoassay procedures have recently been developed which utilize reactions taking place on dry porous carriers such as cellular membranes through which samples to be analyzed can flow by capillary action, the reaction products being detectable either visually or with an instrument such as a reflectometer. While not so limited, these procedures generally involve antigen/antibody reactions in which one member of the reactive pair is labelled with a detectable label. Typically, the label is an enzyme label or a particulate direct label, for instance a sol label such as gold. The art is well aware of many useful labels and their method of operation.

Typical immunochromatographic devices of this nature are described in several United States and foreign patents. For example, U.S. Pat. No. 4,861,711 describes a device in which an analyte is detected by antigen/antibody reactions taking place in a series of coplanar membranes in edge to edge contact. Other devices are described in U.S. Pat. Nos.: 4,774,192; 4,753,776; 4,933,092; 4,987,065; 5,075,078; 5,120,643; 5,079,142; 5,096,809; 5,110,724; 5,144,890; 5,591,645; 5,135,716. All of these patents describe laminated structures.

Devices including cellular porous membranes such as those described in the above identified patents are often difficult to manufacture because they are multi-layer and require several layers of porous materials and filtration strips to insure accurate results.

For detection of cardiac analytes in whole blood, it is necessary to remove red blood cells so that they will not interfere with visualizing or otherwise detecting the colored reaction products normally produced in such immunoassay reactions.

Immunoassay devices when employed to detect cardiac analytes in whole blood utilize labelled antibodies which react with these antigens to produce detectable products. One widely utilized method for such diagnostic or analytical procedures utilizing antigen/antibody reactions employs a labelled detector antibody which reacts with one epitope on the antigen to form a labelled antibody/antigen complex formed in a detection zone of a porous membrane strip. The complex moves along the membrane by capillary action until it contacts a fixed line containing a capture antibody with which it reacts at another epitope on the antigen to concentrate and form a detectable reaction product. Typically, the product is visibly detectable because it is colored.

With some constructions, the color is apparent to the naked eye. In more sophisticated devices, the presence or concentration of the antigen may be determined by measuring the intensity of the produced color or other property of the product with a suitable instrument, for example an optical sensor. The method is utilized in several devices used to detect cardiac analytes in whole blood. In all of these devices, it is necessary to prevent red blood cells from entering the color development or capture area because they interfere with proper visualization of the colored reaction product because of the intense hue of the cells.

Much effort has been expended to prevent such interference. As a result, products of this nature heretofore proposed for analysis of whole blood include some means, such as a type of filter to remove the red blood cells and form a plasma, so that there is no interference with the visibility of the color which is produced.

U.S. Pat. No. 5,135,716 utilizes an agglutinating agent to assist in the separation of red blood cells. Other patents describe the use of paper or plastic filters.

The use of glass fiber fleece is described in U.S. Pat. No. 4,477,575 to filter the red blood cells. Glass fiber fleece, however, simply adds another layer to the device. The principal difficulties arise from the problems of accurately placing several layers of thin flexible strips in proper registry in a laminar structure while at the same time retaining the sample placement zones, reaction zones and other areas of the membrane strips in proper communication with each other. The problems are further complicated by the difficulties of placing the completed membrane in or on a proper platform which is often a hollow casing with separable upper and lower members including fixed pillars and slots to prevent the membrane from moving and to retain selected membrane areas in proper position relative to viewing windows and other openings in the casing.

As a general rule, diagnostic devices such as those discussed above are often described as having an application zone to which the sample to be analyzed is added. The sample flows by capillary action along a predetermined pathway in a substrate, usually a nitrocellulose membrane, to a detection zone. The detection zone carries a mobile, labelled antibody to the analyte sought. If the analyte is present, a labelled antibody/analyte complex is formed which reacts with a fixed, i.e., immobilized capture antibody in a capture zone, downstream of the detection zone, to form a detectable product, usually one which is colored and visible to the naked eye.

It sometimes happens that the labelled antibody/analyte complex forms quite readily but does not sufficiently combine with capture antibody to produce an easily detectable signal. This might happen if no sufficient amount of complex contacts capture antibodies or contacts them in a configuration which is not optimum for forming a detectable reaction product. Other possible problems are insufficient incubation time or low antibody affinity.

These difficulties may be avoided by taking advantage of the biotin/avidin or biotin/streptavidin reaction or analogous reactions well known to the skilled artisan. These reactions are often used to increase the sensitivity of the diagnostic procedure.

In one application of this process, two antibodies are removably deposited in the detection zone and streptavidin is immobilized in the capture zone. The detector antibody is labelled, preferably with a metal such as gold, and reacts with one epitope on the analyte. The other antibody which is labelled with biotin reacts with another epitope on the analyte. The antibody mixture may be considered as a reagent system for use in detecting the presence of the analyte. If analyte is present, a complex containing gold labelled detector antibody/analyte/biotin labelled detector antibody will form in the detection zone. The complex will move through a cellular membrane by capillary action to the capture zone. When the complex reaches the immobilized streptavidin in the capture zone, the streptavidin binds to the biotin and concentrates the complex in a small area to form a detectable reaction product.

There are several known variations of this reaction. For example, the detection zone may contain a biotin labelled antibody together with streptavidin labelled with a colored label such as gold.

The complex which forms and moves into the capture zone is an analyte/biotin labelled antibody/streptavidin gold-labelled complex which will move to the capture zone and concentrate in the capture zone by reaction with a capture antibody to form a detectable reaction product.

The above identified procedures have generally been described to involve reactions taking place on an elongated, rectangular, laminated devices with the sample application zone at one end associated with some type of filter layer. The sample, after filtration, contacts a mobile, labelled specific binding reagent in a detection zone to form a complex which moves along a cellular membrane to a distally placed specific binding reagent, i.e., the capture reagent which is immobilized in a line across the membrane. The complex reacts with the reagent and is concentrated along the reagent line to become visible.

Typically, the sample to be analyzed is placed in the application zone by the addition of several drops to the center of the zone or by dipping the application zone into a small volume of the sample.

There are a number of problems with these configurations, especially when the goal is high sensitivity and the result should be visible within only a few minutes.

High sensitivity can be achieved, for instance, by a capture line in a capture zone having a small width, as compared to the width of the detection zone, so that the amount of labelled reaction product is captured within a small capture area and thereby give a more intense signal color.

Further, the sensitivity can be increased as more labelled volume moves across the capture line during the test procedure. The more labelled volume is needed, however, the greater the area of the detection zone must be.

If this area has the form of an elongated channel and is increased by simply increasing the length thereof, the consequence is a considerable increase in test time, because the velocity of the moving liquid front slows down exponentially with the total distance wetted.

Other shapes of this area (e.g. with a higher ratio of width to length) leading to a large width detection zone and a small width capture zone channel have the disadvantage of creating stagnation regions where there is little or no flow. In extreme cases significant amounts of the sample may never become involved in the reactions which form the detectable product.

Co-pending and commonly-owned application Ser. No. 09/130,164, offers a solution to the above-stated problems. The sample is allowed to enter into the detection zone simultaneously from many different directions and the detection zone is designed in a way that the resulting flow from the different directions all point to the entrance of the capture zone channel and all distances from entering the detection zone to said entrance are essentially the same. This invention alleviates many of the problems aforesaid by providing a device which may be small enough to be hand held, although not necessarily so, and provides for rapid and efficient flow of the fluid to be analyzed. Although its most important present utility is for the analysis of whole blood to diagnose for the presence of cardiac analytes, it may be adapted to test for the presence of other components in a fluid such as a body fluid carrying an antigen which will form a complex with an antibody which may thereafter be detected, for example in a sandwich assay with another antibody. Cardiac analytes as are described in several of the above-mentioned patents may be employed in the emergency room to aid the physician in diagnosing the cause of chest pain and to determine if the pain arises from a cardiac event.

It is towards several improvement in the features of the invention described above that the present application is directed.

BRIEF SUMMARY OF THE INVENTION

The above-described devices have been shown to be especially useful for their intended purposes. The devices of this invention effect several improvements of the earlier devices. For example, they use less of the porous membrane, they can be made smaller so that less material is used in their construction, and they are faster acting. One of its most important advantages, as will be apparent from the following explanation, is that even when a plurality of analytes are to be identified, the only change in structure required is the structure of the porous membrane, and not the supporting layers.

The prior art device, U.S. application Ser. No. 09/130, 164, the full disclosure of which is herein incorporated by reference, provides a solution to the problems as explained herein is that the sample is allowed to enter into the detection zone simultaneously from many different directions and the detection zone is designed in a way that the resulting flow from the different directions all point to the entrance of the capture zone channel and all distances from entering the detection zone to said entrance are essentially the same. Rapid and efficient flow of the fluid to be analyzed can be achieved by configuring the porous channels so that there is little or no opportunity for stagnation and so that the fluid enters a detection zone from a sample circulation channel from a multitude of points. The detection zone is designed so that the resulting front of the fluid moves in the direction of the entrance end of the capture zone.

The improvements herein are directed to the configuration of the device and the interaction between the porous membrane, on which the separation of plasma from blood cells occurs, and the top and bottom layers which cooperate to hold the membrane in the correct position. Furthermore, the top and bottom layers provide channels to conduct the sample from the application hole to and through the membrane to the capture antibodies while carrying out chromatographic separation of plasma from red cells. The first improvement is a reconfiguration of the sample delivery channel such that the fluid is conducted from the application hole to the membrane through a channel comprising the top and bottom layers of the device. In contrast to the prior art device, no membrane is present in the sample delivery channel. The absence of membrane at this location is an improvement in that it reduces the amount of porous membrane required for the device, and avoid concerns regarding the need to eliminate the porosity of membrane located in the sample delivery channel or any concerns regarding contact of the fluid sample with a material other than that comprising the top and bottom pieces (layers) of the device. The resulting product is less costly in both materials and labor to manufacture. The extent of porous membrane required is confined to the detector zone and capture zone. A configured interface between the portion of the device comprising the sample delivery channel, and that containing the membrane and the sample circulation channel, is provided to form a capillary conduit for the blood sample to be channeled to the membrane in accordance with the prior art device, without causing errant distribution of the sample.

A further advantage of this invention is that the same top and bottom layer components of the device are used in the manufacture of a number of different analytical tests. Only the membrane needs to be tailored for the detection of the specific analyte or analytes to be measured. For example, the reagents deposited or bound the membrane and their locations, and the shape of the fluid pathways on the membrane, can be individualized for each assay. The top and bottom layers with the sample delivery channel and sample circulation channel are the same for every assay.

The sample delivery channel may also be configured to contain a predetermined volume of sample, and further, by means of an optional window or transparency, indicate to the user when the sample delivery channel is full and thus adequate sample has been applied. A further improvement is a configuration of the sample delivery channel such that when the channel is full, the sample therein contained is delivered to the sample circulation channel and thereby initiates the immunoassay.

In a further embodiment, reagents such as the labeled detector antibodies may be provided within the channels of the device in the fluid path prior to the membrane, such that the reagents mix with the sample. The reagents may be provided as beads, microbeads, or lyophilized powder, by way of non-limiting examples in the aforementioned channels.

A principal feature of the devices of this invention is that the membrane does not extend the full length of the sample delivery channel. Another is that the sample delivery channel is designed so that a known predetermined volume of sample can be delivered to the operation section of the device.

It is therefore an object of this invention to provide an analytical test device as described above with a sample delivery channel formed in the lower surface of the top layer and with walls defined by the channel and the top surface of the bottom layer. Almost no membrane is present in the region of the sample delivery channel. In one embodiment, the sample delivery channel is configured with parallel sides, and is in operative communication with the sample circulation channel. In another embodiment of the invention, the sample delivery channel is configured to contain the volume of sample needed to carry out the analysis in the device. In this embodiment, the end of the sample delivery channel which is in operative communication with the sample circulation channel is shaped to provide a narrowing of the sample delivery channel where it meets the sample circulation channel. In this embodiment, when the sample delivery channel has filled with fluid up to the point where the fluid contacts the narrowed section, capillary action will channel the fluid from the sample delivery channel to the sample circulation channel, and then onto the membrane of the device. The sample then flows until the sample delivery channel drains of its predetermined volume, and the analysis is performed. As mentioned above, an optional observation window at the junction of the sample delivery channel and the sample circulation channel may be provided to indicate to the operator that adequate sample has been added to the device to conduct the test, as when the sample delivery channel has filled completely with blood and the sample is channeled to the sample circulation channel, the observation window will indicate the presence of the sample.

As in the case of the co-owned application referred to above, the invention described herein alleviates the problems with the prior art device because the sample is allowed to enter into the detection zone simultaneously from many different directions and the detection zone is designed in a way that the resulting flow from the different directions all point to the entrance of the capture zone channel and all distances from entering the detection zone to said entrance are essentially the same. Rapid and efficient flow of the fluid to be analyzed is achieved by configuring the porous substrate (membrane) so that there is little or no opportunity for stagnation and so that the fluid enters a detection zone from a sample circulation channel from a multitude of points. The detection zone or channel is designed so that the resulting fluid front moves in the direction of the entrance end of the capture zone channel.

The devices of this invention and their advantages will be better understood by reference to the structures utilized in the previous application. Accordingly, the structures of both inventions will be described in some detail in connection with the following drawings.

BRIEF DESCRIPTION OF THE DRAWINGS

FIGS. 1A–D is a representation of a device of the invention described in Ser. No. 09/130,164.

FIGS. 4, 5, 6 and 7 are sectional views along the lines A—A, B—B, C—C and D—D, respectively, of FIG. 3A.

The cross-hatched top portion represents the cross-sectional portion of the top layer of the device, the open bottom portion represents the cross-sectional portion of the bottom layer.

Figure 8:
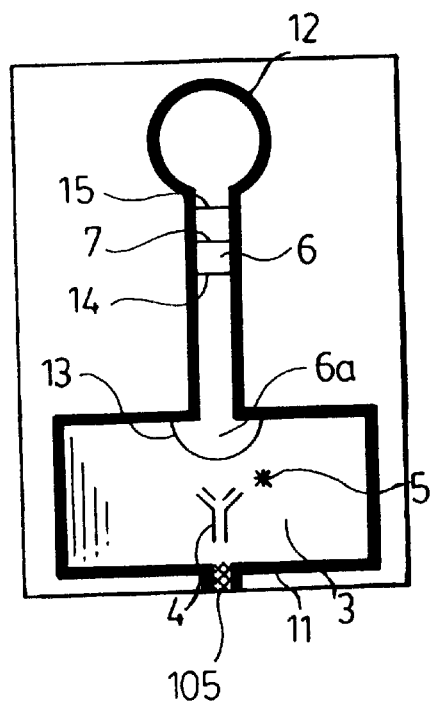

FIG. 8 shows a membrane configuration of a device of this invention for detecting one or several analytes with one rectangular detection zone and one narrow capture zone channel.

Figure 9:
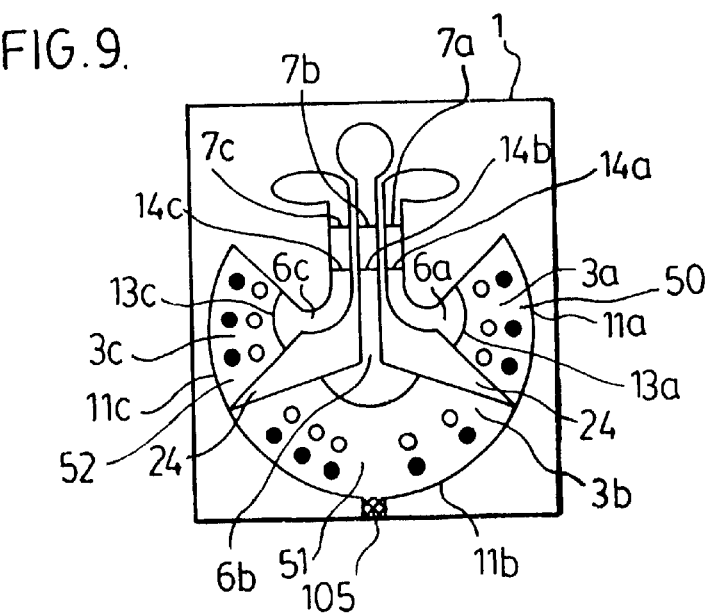

FIG. 9 shows the configuration of a presently preferred membrane of this invention suitable for the detection of three different analytes via the biotin/streptavidin route.

Figure 10:
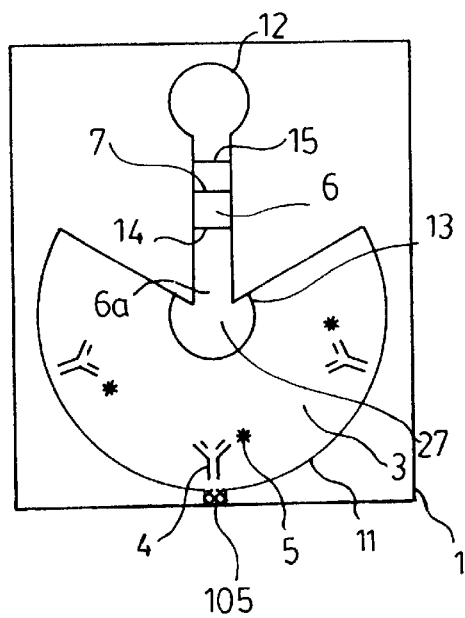
Figure 11:
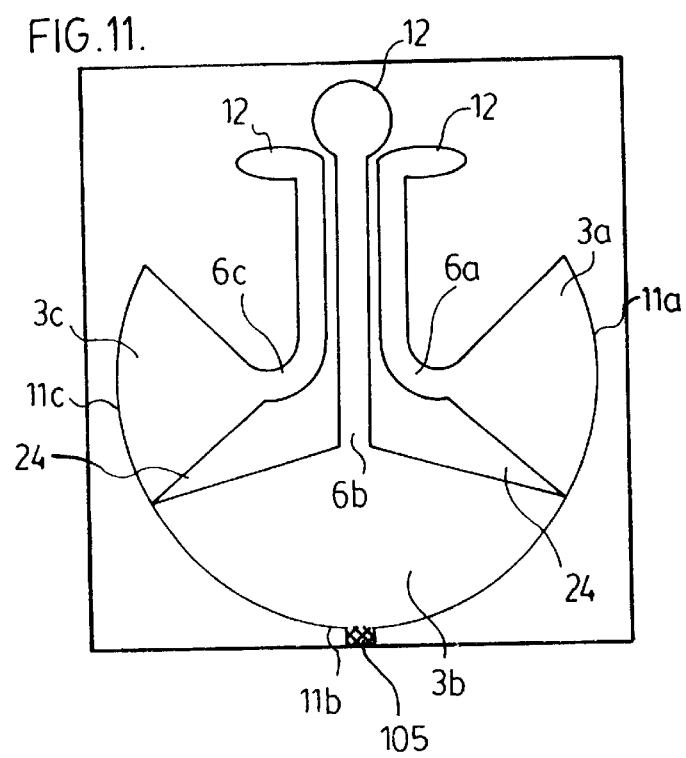

FIGS. 10 and 11 show the configurations of alternative porous membranes with one and three fluid pathways, respectively.

FIGS. 12A–B shows a configuration of the bottom surface of the top layer of a device of this invention which includes a sample delivery channel of a predetermined volume with a window to indicate that the channel is full, and a construction which channels the fluid from the sample delivery channel to the sample circulation channel. A cross-section of the top layer of the device at section lines E—E is shown in FIG. 12B.

Figure 13:
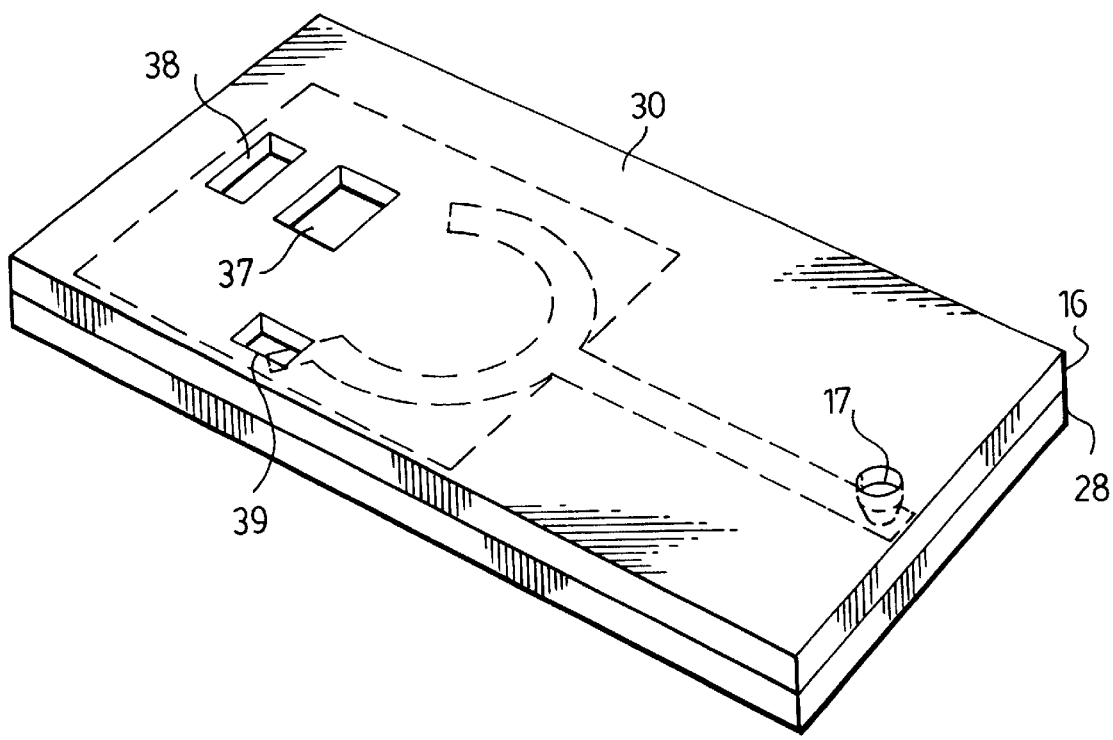

FIG. 13 is a perspective view of a device of this invention.

FIGS. 14A, 14B and 14C represent an exploded view of a device of this invention with a top member, a support member and a porous carrier in a configuration of FIG. 9.

GLOSSARY

The following terms have the following general meaning as they are used in this specification and claims.

"Dry porous carrier" and "dry porous carrier layer" refer to a cellular product through which the sample to be analyzed can move by capillary action. As will be seen by the figures and understood by the description of the invention, the dry porous carrier (layer), which in this art is often referred to as a membrane, is configured by closing off some of the porous areas so that the fluid to be analyzed moves along defined pathways through selected channels. "Top layer or top piece" is a layer in the analytical test device which is configured to cooperate with a bottom layer or bottom piece to hold the dry porous carrier (membrane) layer when the top and bottom layers are placed in registry to provide, in cooperation with the dry porous layer, pathways which control the direction of flow of the sample to be analyzed through the device.

"Antigen" is a molecule which, in an animal, induces the formation of an antibody. The devices of this invention are useful for determining the presence of antigens in a fluid. They are especially useful for analyzing body fluids particularly whole blood, serum, plasma and urine. Antigens are often referred to as "analytes".

"Cardiac analytes" are analytes which are released into the blood as a result of cardiac tissue deterioration.

"Channel" is any formed conduit through which the fluid sample under analysis flows in the analytical test device. A channel may be formed in the top layer or in the porous carrier layer itself . Since the top layer is generally a rigid plastic such as a polyacrylate or polymethacrylate, a channel may be formed by molding, stamping, machining or any equivalent process. In the porous layer, the channels may be formed by stamping the desired configuration into the layer. They may also be designed into the porous layer by forming non-porous boundaries with wax or ink. Channels are said to be in an operative communication when a fluid in one channel flows directly into another.

"Semicircular", as the word is used herein is not limited to one half of a circle, but generally refers to a circle area where a sector has been removed or to this sector itself.

"Circumscribed", as the word is used herein is not limited to an arcuate channel surrounding and conforming to a semicircular area of a porous membrane. The term includes—as will be apparent as this description continues—other configurations in which a sample circulation channel conforms with the border of one or more detection zones of other configurations, for instance when the area of the carrier is polygonal or forms part of a polygon.

"Essentially" is a term used in connection with the distances between the points of sample entry into the detection zone and the entrance end of the capture zone channel. These distances should be as similar as possible. Obviously, a semicircular area on the carrier to which an arcuate sample circulation channel conforms is a highly preferred configuration because all resulting distances between the arcuate border of the detection zone and the entrance end of the capture zone channel are the same.

"Rapid" means that a detectable product forms within a sufficiently short period of time, e.g. within about 5 to about 15 minutes, to permit the medical attendant to draw meaningful and useful conclusions.

"Efficient" means that a detectable product can be formed with a low volume of fluid, e.g. a few drops of whole blood (from about 10 $\mu$l to about 80 $\mu$l), utilizing small amounts of reagents even when the antigen is present in very low concentrations as is usually the case with the cardiac analytes such as troponin I.

Figure 1A:
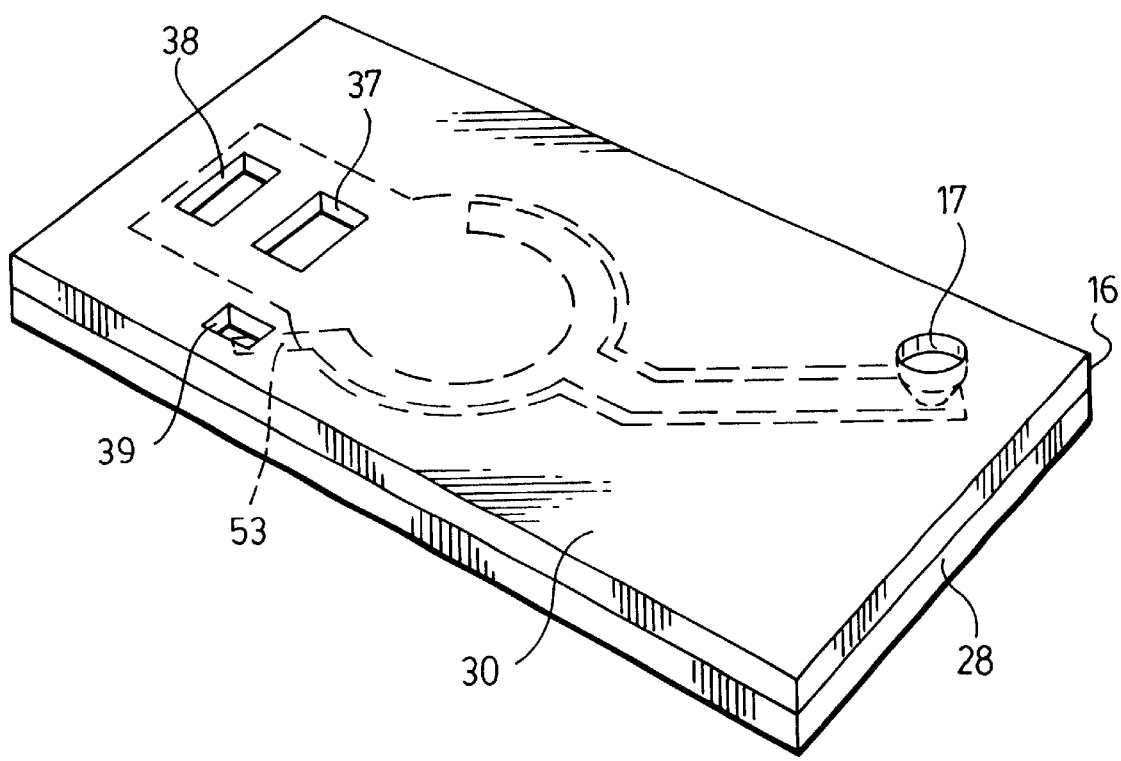

In the figures, like numbers have similar meanings. FIG. 1A is a perspective view and FIGS. 1B, 1C and 1D an exploded view of the invention of the previous application showing a top layer 16, a support layer 28, with a porous carrier 1 having a plastic backing layer 29 sandwiched between them. Through hole 17 runs from the upper surface 30 through to the bottom surface 31 of the top layer 16 in registry with a sample delivery channel 18 formed in the bottom surface 31 of the top layer 16. Sample delivery channel 18 is in operative communication with a sample circulation channel 19 also formed in the bottom surface 31 of top layer 16. The circulation channel 19 is closed at both ends as shown by numeral 20. The circulation channel 19 is formed with inner walls 21 and outer walls 22. As shown in FIG. 1B, inner walls 21 form the boundary of an indent formed in the bottom surface 31 of the top layer 16, referred to as capillary trap 23. Capillary trap 23 is shown extending into the area 33, but it is not necessary that it does so.

Referring further to the figures, top layer 16 is attached to the support layer 28 by pins 34 which may be force fit into corresponding holes 35. Any other equivalent means of attachment may be employed and the two layers 16 and 28 may be permanently or removably fixed.

Porous carrier 1 is shown in FIG. 1C with a backing 29 such as a polyester film. It is held between support layers 16 and 28. The carrier 1 may have the same exterior dimensions as layers 16 and 28 so long as there is an operative pathway through which the fluid added by way of through hole 17 can pass through the delivery channel 18, the circulation channel 19, the detection zones 50, 51 and 52, and the capture zone channels 27a, 27b and 27c to the closed ends 20 and 12, of circulation channel 19, and of the capture zone channels 27a, 27b, and 27c, respectively. The porosity of the portion of the porous carrier 1 situated in contact with the sample delivery channel 18 is destroyed in order to prevent the flow of sample in the membrane. The porous membrane 1 shown in FIG. 1C is configured for the detection of three analytes. Accordingly it contains three detection zones or channels 50, 51 and 52, communicating with three capture zone channels 27a, 27b and 27c, respectively. The contiguous arcuate border 11 of the detection zones 50, 51 and 52 extend over the inner walls 21 of circulation channel 19 so that the flow of fluid when stopped at ends 20 will flow by capillary action into the detection zones 50, 51 and 52.

Referring further to FIG. 1, the flow is stopped at the ends 20 of the circulation channel to make it possible to control the size of the sample. An optional window 39 over an optional extension of the sample circulation channel shown as a dotted structure 53 in FIGS. 1A and 1B, may be provided to indicate that adequate sample has been applied to fill the channel. The corresponding portion of the carrier 1 is blocked out to limit flow to the optional channel, as well as the corresponding portion of the carrier beneath the sample delivery channel. A further advantage of the design of the device of the invention is that the same top and bottom layer pieces may be used for a variety of different devices.

If the top layer 16 is transparent, the formation of a visible reaction product will be readily apparent. If the top layer 16 is opaque it will be constructed with one or more viewing windows, shown in this example with a single window 37, and a test end indicator window 38. These one or more windows as shown in FIG. 1A will be in registry with the capture zone channels so that the operator can view the formation of colored products or adjust an instrument such as a reflectometer to determine if a detectable reaction product has formed.

Figure 2:
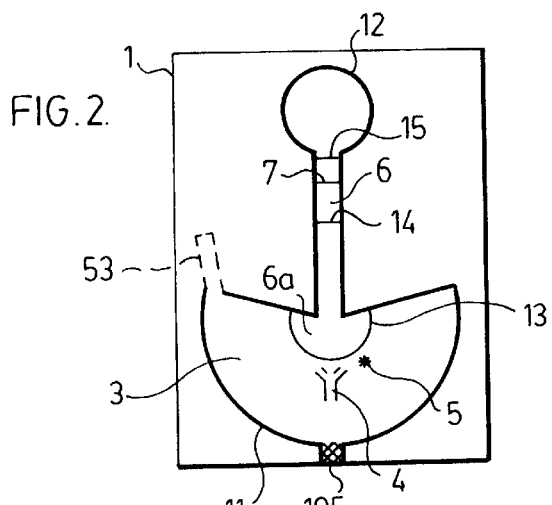
FIG. 2 shows a membrane configuration for use in a device of this invention which is suitable for detecting one or several analytes with one semicircular detection zone and one narrow capture zone channel. The border of the semicircular detection zone will connect to a sample circulation channel.

A optional test end indicator window 38 is provided to indicate when the test is over by, for example, the presence of a dye in the porous carrier 1 upstream from the test end indicator window 38 but downstream from the portion of the porous carrier 1 under window 37 and the capture zone(s) 7. The dye is carried to the test end indicator window when sample has passed the capture zone. In another embodiment, as shown in FIG. 2, the capture zone channel 6 may optionally contain a product 15 which reacts with any substance normally present in blood, plasma, serum or other body fluid to produce a visible product. This configuration may be provided on the porous carrier 1 either in window 37 or in the test end indicator window 38.

The device depicted in FIG. 1A has a single window for viewing the capture zone and a test end indicator window for purposes of illustration. In preferred devices, there will be one window extending transversely of the top surface 30 so that the results of all of the reactions can be viewed at once.

It will be noted from FIGS. 1A–1D that the dimensions of the sample delivery channel 18 are uniform throughout its length and that the membrane 1 extends well into the delivery channel. It is also noted that the porosity of the portion of the membrane situated under the sample delivery channel 18 is destroyed to prevent the sample from spreading along the porosity of the membrane.

DETAILED DESCRIPTION OF THE INVENTION

As mentioned above, the devices of this invention may be employed to analyze a variety of liquid samples, especially biological samples which can be analyzed by conventional antigen/antibody reactions of either the competitive or sandwich variety utilizing labelled reactants which emit a detectable signal. The skilled artisan will recognize that there are several applications of the device of the invention.

It is presently contemplated that the invention will find its principal utility for the diagnosis of whole blood for the presence of cardiac analytes such as troponin I, troponin T, myoglobin, CK-MB, myosin light chain, fatty acid binding protein, glycogen phosphorylase BB, actin and any of a host of other known analytes which are found in the blood as cardiac tissue deteriorates following an ischemic event such as angina or myocardial infarction. Accordingly, the invention will be principally described as utilized in the diagnosis of cardiac events. However, the device may be adapted for use to detect a wide variety of analytes by immunologic and other assay formats that take advantage of the separation of plasma from red blood cells in a chromatographic fluid flow of the device of the present invention. In fact, and as will be seen below, a single device may be configured to perform a plurality of assays of more than one format, for example an immunoassay and an enzyme-based assay, by providing the particular assay components in each of the separate fluid paths available in the device.

The structures of the invention are especially useful for analyzing blood, serum and plasma for creatine kinase MB CK-MB, myoglobin, myosin light chain, troponin (TNI) I, troponin C, troponin T, and complexes of troponin I, troponin C, troponin T containing at least two troponin subunits as described in U.S. Pat. Nos. 5,747,274; 5,290,678; and 5,710,008, the entire contents of which are incorporated herein by reference.

It will be noted from FIGS. 1A, 1B, 1C and 1D that the delivery channel 18 of the previous device is angled just below the entry into the circulation channel 19. This makes it possible to shorten the overall length of membrane 1. It will also be noted that there is an extension of the porous carrier 1 which extends the full length of the sample delivery channel 18.

It has now been discovered that the length of the porous carrier (membrane) 1 can be reduced to only extend from the portion under the sample circulation channel as far as is necessary to define a fluid path from the sample delivery channel 18, to the sample circulation channel 19 and onto the membrane. Any small extension 105 of membrane 1 needed to extend into the sample delivery channel has its porosity destroyed such that the sample does not flow across the membrane, and that the fluid pathway is from the sample delivery channel to the sample circulation channel and then onto the membrane.

The sample delivery channel 18 can be either straight or contain an angle.

Another advantage of the device of this invention is that the section of the delivery channel 18 entering the circulation channel 19 can be reduced in cross section so that there will be capillary movement of the sample into that section of the sample delivery channel 18 having the smaller dimension. The particular advantage of this configuration is that the section of the sample delivery channel 18 having the larger volume can, in fact, be designed to hold the exact volume of sample needed to conduct the analysis.

Judicious placement of viewing windows as explained below will permit the operator to be in complete control of the whole operation.

As noted above, one improvement of this invention is a reduction in the size of the porous carrier 1 of the device, reducing the cost and avoiding the need of eliminating the porosity of the portion of the membrane in contact with the sample in the area of the sample delivery channel 18, for example, by printing with a special ink. A further improvement is a sample delivery channel with a volume delivery means as described above, wherein once the sample delivery channel 18 is filled to its predetermined volume with sample, the complete sample volume empties into the sample circulation channel 19 to initiate the immunoassay. An optional window 91 at or near the junction of the sample delivery channel and the sample circulation channel 19 serves to indicate that adequate sample has been applied to the device.

FIG. 2 illustrates a dry porous carrier layer 1 (also referred to as membrane 1) of the invention configured for the analysis of whole blood for one analyte or a plurality of analytes by reactions between the analyte(s) and antibody pairs which react with different epitopes on the analyte in the classical antigen/antibody reaction utilizing polyclonal or monoclonal antibody pairs, one member of the selected pair being labelled.

The figure shows carrier layer 1 in which the porosity of a selected section or demarcated boundary of the layer has been destroyed to leave a defined porous area comprising a semicircular detection zone 3 with a border 11 and capture zone channel 6 which is closed at terminal end 12. Border 1 1 includes a small extension 105 which, in the assembled device, is in registry with the junction thereabove between the sample delivery channel 18 and the sample circulation channel 19, as will be clearly seen in the cross-sectional view in FIG. 5. This extension 105 will be in contact with the fluid to be analyzed. Its porosity is destroyed. The portion of the membrane, and attendant extension 105 that extends beyond the sample circulation channel towards the sample delivery channel may be reduced to a very small size, or eliminated entirely, provided that the channels and corresponding structures which hold the membrane in position define the fluid path from the sample delivery channel to the sample circulation channel and then onto the membrane. The various capillary traps and cavity described herein cooperate to maintain this defined fluid pathway. Other variations of these parts which achieve the aforesaid fluid pathway are embraced within the invention herein.

This membrane 1 which for analysis of whole blood is preferably nitrocellulose or equivalent material which chromatographically separates red blood cells to form a red blood cell front 13 and a plasma front 14 downstream thereof. For the analysis of other liquid samples, other materials may be preferable.

The detection zone 3 contains detection antibody 4 with detectable label 5 which reacts with the analyte, if present, to form a labelled antibody/antigen complex.

Although, for convenience, only one antibody is shown, the detection zone 3 may contain several labelled antibodies.

Antibody 4 is mobile, i.e., it is movably deposited in the detection zone 3 by any of several known means so that the labelled antibody/analyte complex once formed is free to move downstream into the capture zone channel 6 for reaction with the capture antibody 7 fixed transverse of the capture zone channel 6 to form a detectable reaction product.

Again, for convenience, only one capture antibody line 7 is shown, but there may be a plurality of such lines, one for each analyte to be detected.

Capture zone channel 6 may optionally contain a product 15 which reacts with any substance normally present in the fluid to be analyzed to produce a visible control product. The use of a control reaction is optional, but is preferred. This reaction indicates that the fluid has passed the capture zone, and functions as a test end indicator.

The dry porous carrier layer 1 (also referred to as membrane 1) need only be large enough to comprise the components shown in FIG. 2, and does not need to extend to the portion of the device comprising the sample delivery channel. As will be seen below, the present device may be configured to accommodate the smaller dry porous carrier layer 1, and still achieve the objects of the invention. By reducing the amount of dry porous membrane required for the device, the cost of materials is reduced. Further advantages of the reduced size of the dry porous carrier layer will be noted below, particularly, in the absence of membrane in the sample delivery channel.

Figure 3A:
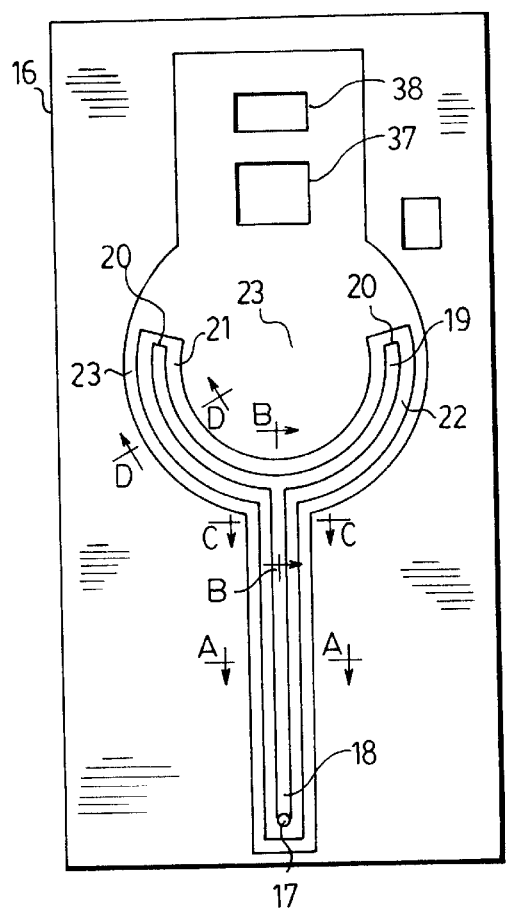
FIGS. 3A–B shows the configuration of the lower surface of the top layer and the top surface of the bottom layer, respectively, of a device of this invention suitable for use with the membrane of FIG. 2. Cross-sectional lines A—A, B—B, C—C, and D—D are shown in subsequent figures, representing the cross-sections through the assembled device.
Figure 3B:
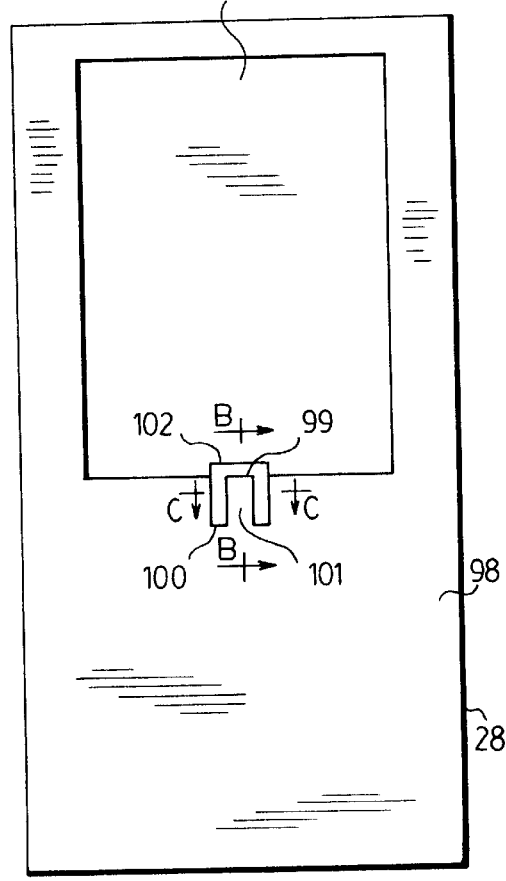

FIG. 3A shows the configuration of the lower surface 23 of the top layer 16 which will be brought into registry with the top surface of bottom layer 28, shown in FIG. 3B, with membrane 1 of FIG. 2 therebetween in area 103, to provide one embodiment of the invention.

The top layer 16 has a through hole 17 for application of the sample. It is in operative communication with sample delivery channel 18 which communicates with sample circulation channel 19. Sample delivery channel 18 has walls defining the channel, and a capillary trap 23 beyond the walls to confine the sample to the channel and prevent the sample from flowing between the apposed bottom surface of the top layer and the top surface of the bottom layer. This is shown in cross-section in FIG. 4. Sample circulation channel 19 is shown in an arcuate configuration in order to conform with the border 11 of the semicircular detection zone 3 of FIG. 2.

Sample circulation channel 19 is closed at both ends 20. It is formed with inner wall 21 and outer wall 22 and is surrounded by a capillary trap 23 which functions to assure that the flow of sample is into the detection zone 3 of FIG. 2 at all points of border 11, and then into the capture channel 6 at its entrance end 6a.

FIG. 3B shows the configuration of the top surface of bottom layer 28. A flat rectangular area 103 recessed into the top surface 98 of the bottom layer 28 holds the membrane 1. The depth of area 103 from the top surface 98 is sufficient such that the top surface of membrane 1 is at the same level as top surface 98. Other configurations of area 103 are contemplated by the present invention, such as it extending to the borders of the top section 28. In another embodiment, no recess is provided but the top layer 16 and bottom layer 28 are configured to hold the membrane 1 in the correct orientation. It is only necessary that the top and bottom layers come together with the membrane in between to define the fluid path from through hole 17 to the end of the membrane channel 12. The thickness of the various channels may be adjusted accordingly.

Membrane 1 is positioned to contact surface 99 of a cavity 102 located at the interface between the sample delivery channel 18 and the sample circulation channel 19. FIG. 14C shows this cavity in a three-dimensional representation to assist in conveying the relationship between the parts of the device, as well as its function. When the top layer 16 and bottom layer 28 are aligned for operation of the device, the sample delivery channel in the bottom surface of the top layer 16 passes along extension 101 until it meets circulation channel 19. The relative positions of cavity 102, the junction of the membrane with edge 99, and the junction of the sample delivery channel 18 and sample circulation channels 19 thereabove form a conduit such that the fluid flows from the sample delivery channel 18 into the sample circulation channel 19 above the membrane. The flow of fluid is confined to the sample circulation channel 18 and onto the membrane 1 because the contact between membrane 1 and edge 99 is isolated by air from other surface contacts that may provide alternate capillary conduits for the fluid. The walls of the sample delivery channel 18, surrounded by a capillary trap 23 and extending from the through hole 17 towards the sample circulation channel 19, extend along extension 101 such that the capillary trap 23 of the lower surface of top layer 16 corresponds with the portion of cavity 102 of the top surface of bottom layer 28. These relationships will be further explained by reference to the cross-sectional views and FIGS. 4–7, below. As such, the walls and capillary trap end at an air junction, also preventing the fluid from flowing beyond the walls of the sample delivery channel 18, leaving the fluid to continue to flow by capillary action to the sample circulation channel 19.

FIGS. 4, 5, 6 and 7 are sectional views along the lines A—A, B—B, C—C and D—D, respectively, of FIG. 3A. Like numerals have the same meaning. Dimensions [mm] are merely for illustration. Dimensions do not fit to scale. FIG. 4 shows the sample delivery channel 18, formed as a capillary recess in the top layer 16, further defined by a bottom wall formed from the apposing portion of the top surface of the bottom layer 28 of the device, and further defined by walls on each side which are further surrounded by a capillary trap 23 to contain the flow of fluid within the channel. The extent of the dimensions of the capillary trap on either side of the channel is optional, and may extend to or nearly to the perimeter of the top layer.

FIG. 5 shows a longitudinal section along the direction of the sample delivery channel 18 where it meets the sample circulation channel 19, and further shows the position of the membrane thereunder and its contact with edge 99 of cavity 102 (as referred to in FIG. 3B). As described above, the membrane is positioned such that the only conduit from the sample delivery channel is into the sample circulation channel and then onto the membrane, as no other possible conduits from the sample extend from this area, other than the thickness of the walls of the sample circulation channel 18, defined by capillary traps 23 on both sides, as described further below. The bottom of the sample delivery channel is in contact with the edge of the membrane only at edge 99 as shown in FIG. 3B, and thus the membrane is isolated by air from contact with any other parts of the device by virtue of cavity 102 extending below and to the sides of extension 101 of the top surface of the bottom layer 28. Thus, fluid flow is limited to the defined channels. The small extension 105 of the sample circulation channel as shown in FIG. 2 corresponds to the portion of the membrane 1 that extends under the sample delivery channel at its junction with the sample circulation channel 19 and abuts edge 99 of cavity 102. This extension may be open, or preferably blocked by having its porosity destroyed, for example, by printing with a special ink. Its purpose is to prevent the blood from moving outside of the defined sample pathway on membrane 1, and to define the fluid pathway from the sample delivery channel to the sample circulation channel and then onto the membrane.

FIG. 6 represents a cross-sectional view across the device at the level of the sample delivery channel 18 at the position where it extends over extension 101 into cavity 102 (as referred to in FIG. 3B). The cavity 102 in combination with capillary trap 23 cooperate such that the fluid conduit is confined to the sample delivery channel 18, where it subsequently meets the sample circulation channel 19 over the membrane 1. The width of the walls of sample delivery channel 18 are confined within the width of extension 101, such that the outer edge of the walls meet capillary trap 23 and cavity 102, preventing any fluid flow beyond the thickness of the walls of the sample delivery channel 18. The width of the capillary traps 23 on the exterior of the sample delivery channel 18 may be varied in the construction of the device.

FIG. 7 shows a cross section of the sample circulation channel 19. This is the same as that described in co-pending application Ser. No. 09/130,164, incorporated herein by reference. In operation, the sample enters the sample circulation channel 19 and rapidly moves by capillary action to the ends 20 of the sample circulation channel 19. Once the channel is filled, the sample contacts the membrane 1 all along the sample circulation channel 19 and passes onto the membrane essentially simultaneously from the entire arc of the sample circulation channel 19 onto border 11 and into the detection zone 3.

FIG. 8 is similar to FIG. 2 except that the detection zone 3 is rectangular in configuration and the sample circulation channel 19 which circumscribes the border 11 is similarly rectangular. As with FIG. 2 the device is shown with one mobile, labelled, detection antibody 4 and 5 and one fixed capture antibody 7. The device of FIG. 8 can be employed to detect one or more than one analyte provided that there is no substantial amount of cross reaction.

FIG. 9 shows the configuration of a presently preferred membrane 1 of the invention in which the biotin/streptavidin reaction is utilized to diagnose a whole blood sample for the presence of three analytes. It is as described in co-pending application Ser. No. 09/130,164, with the exception of the small extension 105 at the portion of the membrane 1 in contact with the junction between the sample delivery channel 18 and the sample circulation channel 19. The configuration of the channels in the top layer can be readily understood from the foregoing and following explanation. In the figure like numerals have the same meaning as in the other figures. The design may be employed to ascertain the presence of several analytes such as myoglobin, troponin I or T and CK-MB in one small sample.

The membrane 1 is formed with three distinct pathways, one for each analyte leading from the borders 11a, 11b and 11c of three separate detection zones 3a, 3b and 3c. The detection zones are separated by blocking segments 24. The whole operative area is configured so as to provide three detection zones 3a, b and c in operative communications at their borders 11a, 11b and 11c with the sample circulation channel 19 on the lower surface of the upper layer 16 of the device. The detection zones 3a, 3b and 3c are in operative communication with the corresponding entrance ends 6a, 6b and 6c of the respective capture zone channels.

The detection zone 3a contains two labelled antibodies, e.g. a biotin labelled antibody to CK-MB and a gold labelled antibody to CK-MB.

Generally, in FIG. 9 black circles stand for gold labelled antibodies while open circles stand for biotin labelled antibodies. No reference numerals are given for these detector antibodies in order not to clutter this figure.

As an example of the separation of the plasma from red blood cells during the operation of the device of FIG. 9, the red blood cell front in each of the three detection zones 3a, 3b, and 3c is shown as 13a, 13b, and 13c, respectively; the location of the respective plasma fronts are shown as 14a, 14b, and 14c, respectively.

If CK-MB is present in the sample, the complex which forms will enter the capture channel at entrance 6a to ultimately react with streptavidin at the streptavidin line 7a to produce a visible product.

Analogous reactions take place with other analytes such as troponin I or troponin T and with myoglobin in the separate pathways shown in the figure. The same or other analytes may be similarly detected with conventional antigen antibody reactions.

FIGS. 10 through 14c are provided to further explain the invention and to show its versatility.

FIG. 10 illustrates a porous carrier layer 1 of the invention configured for the analysis of whole blood for one analyte such as troponin I. The figure shows the porous carrier layer 1 in which the porosity of the layer has been destroyed in some areas to define detection zone 3 and capture zone channel 6 which is closed at terminal end 12. The membrane 1 which is preferably nitrocellulose or equivalent material chromatographically separates red blood cells to form a red blood cell front 13 and a plasma front 14. In this embodiment of the invention, the detection zone 3 contains a labelled detection antibody 4 which is constructed with label 5. The antibody reacts with the analyte, if present, to form a labelled antibody/antigen complex.

The labelled antibodies 4 are mobile, i.e., they are movably deposited by any of several known means in the detection zone 3 so that the labelled antibody/analyte complex once formed is free to move downstream into the capture zone channel 6 for reaction with a capture antibody at line 7 fixed transverse of the capture zone channel 6 to form a detectable reaction product.

Capture zone channel 6 may optionally contain a product 15 which reacts with any substance normally present in blood, plasma, serum or other body fluid to produce a visible product. The use of a control reaction is optional, but is preferred so that the operator will know that sufficient blood or other fluid has been applied to the device to permit diagnostic reactions to take place.

It will be noted that detection zone 3 and capture zone channel 6 are in operative communication, i.e., fluid in detection zone 3 will flow by capillary action directly into capture zone channel 6 through the entrance end 6a.

It will also be noted that the detection zone 3 has a semicircular geometry and thus an arcuate border 11. The center of this arc where detection zone 3 is in operative communication with the capture zone channel 6 can be considered a second or opposite end 27 of the detection zone 3 through which fluid can flow into the entrance end 6a of the capture channel 6. As a result of this configuration, every point on the border 11 is equidistant from the entrance end 6a of the capture zone channel 6 and all of the fluid in the detection zone channel 3 flows uniformly into the capture zone channel 6 with successive segments of the sample reaching the entrance end 6a at substantially the same time. This uniformity of flow from several directions will be more clearly understood in connection with the description of the top layer which appears herein.

A major feature of the device of this invention is that when the plasma stream which flows through the detection zone 3 and capture zone channel 6 and reaches the capture antibody line 7, there is little or no labelled antibody/antigen trapped in the detection zone 3 as in the prior art constructions. Instead there is rapid and efficient capillary flow of the fluid from the detection zone 3 to the capture channel zone 6. The capture antibody 7 reacts with and concentrates the labelled antibody/analyte complex to form the detectable product with maximum efficiency. One advantageous result of this novel configuration is that the size of the diagnostic device can be reduced to a minimum.

Any of a variety of labels available to the skilled artisan may be utilized in the devices of this invention. Metal and enzyme labels are preferred. Metal labels are especially preferred due to their remarkable sensitivity. Amongst the metals, gold is most preferred principally because it is so widely employed for this type of reaction and its character-istics are so well understood. Additionally, a gold signal can be enhanced to become more readily visible by the use of a soluble silver salt and a reducing agent in accordance with known procedures. The gold label acts as a catalyst to reduce the silver salt to metallic silver, which deposits as a visible product. A typical reactive pair is silver lactate, which serves as the source of reducible silver ions, and hydroquinone as a reducing agent. The metallic silver forms a readily discernible black deposit around each particle of gold.

The preferred particle size for gold labelled antibodies used in the invention is from about 35 to 65 nm, although appreciable variation can be tolerated depending on well understood factors such as the concentration of the analyte and the affinity of the reactants.

If an enzyme label such as horseradish peroxidase is employed, reaction may be detected by the addition of hydrogen peroxide and a dye such as ortho phenylenediamine in accordance with standard procedures.

There may be a preincubation zone in the detection zone although it is not a necessary feature of the invention. The preincubation zone is employed to remove products present in the blood which may interfere with the desired reactions or make them difficult to detect. For example, if the device is to be used to detect cardiac analytes a typical interferant is the isoform of creatine kinase, CK-MM. Antibodies to the isoform CK-MB may cross react with CK-MM and give false readings. This can be avoided by providing sufficient immobilized antibody to CK-MM in a preincubation zone upstream of the mobile antibody for CK-MB so that all of the CK-MM is removed before the moving sample reaches the detection antibody.

The device of FIG. 10 may utilize one or a plurality of labelled detector antibodies and capture antibodies in immobilized capture antibody lines. When several labelled detectors are employed care must be exercised to avoid interfering cross reactions. It is often best that the antibodies be arranged in more than one detection zone to react with their specific analytes as explained below in connection with the other figures.

The device of FIGS. 10 and 11 may also be prepared to employ the biotin/avidin reaction utilizing variations such as those described above. In the presently preferred variation as applied to the device of FIG. 13, a biotin labelled antibody and a gold labelled antibody are movably placed in the detection zone 3, where each of them reacts with a different epitope on the analyte to form a ternary complex composed of biotin labelled antibody/analyte/gold labelled antibody which moves by capillary action into and through the capture channel zone 6 where it reacts with avidin or streptavidin to concentrate and form a detectable reaction product.

Of course, the antibodies employed in this invention may be either monoclonal or polyclonal. Similarly equivalents of the biotin/avidin reaction can be employed. All of the reagents mentioned herein may be replaced with equivalents and are illustrative but not limitations of the invention.

The skilled artisan will recognize that any porous substrate that chromatographically separates red blood cells and plasma from whole blood may be employed in this invention. However, nitrocellulose is preferred because it is readily available at reasonable cost. Nitrocellulose has been employed in chromatography and related fields for so many years that scientists and technicians are familiar with its properties. Commercially available nitrocellulose sheets can be readily formed into any selected formation with any selected configuration of channels.

The nitrocellulose membranes of the invention may be characterized as sponge-like with a plurality of interconnected micropores of various sizes and dimensions giving rise to capillary forces within the membrane. This permits the biological fluid under investigation to move along the selected pathway.

For the separation of plasma from red blood cells in the practice of this invention, the area, geometry and dimensions of the various devices are so selected that the desired reactions take place in preselected areas as the liquid sample moves along predesigned pathways. For cardiac diagnosis of whole blood, these areas are selected on the basis of the relative speeds of the fronts of the red blood cell stream and the plasma stream, the kinetics of the desired reactions, the affinity of the antibodies for their respective epitopes and other factors which are well known to the skilled artisan or readily determined by conventional testing procedures.

FIG. 11 shows the configuration of an alternate porous membrane with three fluid pathways, for use with three analytes. The configuration and operation of the membrane will be apparent from the explanation of the operation of the other devices.

While, as aforesaid, it is preferred to design the diagnostic devices of this invention to detect more than one analyte, it is possible to design them with a single capture channel and multiple capture lines, one for each analyte, or with a plurality of capture channels each with a single capture line. This latter design, however, is not preferred because of the need for increased sample volume to ensure that reactions will take place in all channels. This defeats a principle aspect of the invention, namely to use the smallest sample with which it is possible to obtain useful results.

A compromise which to some extent, but not completely alleviates the problem is to make the channels as small as possible and design them to be as close as possible to each other. The proximity of the channels, however, increases the difficulty of reading the results with confidence because it is difficult to distinguish a capture line in one channel from a capture line in another.

The devices of the invention can be configured with multiple channels to have more than one channel including the test channel and/or a negative and positive control channel. Multiple channels may each have more than one capture line. The designs will be readily apparent to the skilled artisan.

One channel, usually the middle channel will contain only fixed antibodies to the suspected analyte(s). The positive control channel will contain mobile labeled antibodies at the entrance to the channel and fixed antibodies deeper in the channel. The negative control channel will contain fixed antibodies, but will be blocked at its entrance to prevent the sample under test from entering. The negative test channel will be designed with an entrance hole through the support member to permit the addition of an analyte free material such as a buffer which will migrate to the capture antibodies.

The products and procedures of the invention, in addition to their value to test for cardiac analytes as described in detail above, may also be usefully employed in other medical procedures such as pregnancy and ovulation tests. They are especially useful to test for infections caused by particular viruses. For this utility they can be designed for both competitive and sandwich assays. They can be used to test for antigens, antibodies, surface antigens, and virus particles such as gp120 of the AIDS virus.

Additionally, the products can be employed to test for drugs including drugs of abuse.

The reactions conducted in the various diagnostic procedures employed in the practice of this invention are generally well known to those skilled in the art. Most of them are ELISA tests conducted in a new and useful format. The advantages of this invention is that it provides new and useful formats on which the reactions can be conducted on small, hand-held instruments with speed and efficiency using low volumes of test liquids while concurrently enabling the operator to have great confidence in the results.

While the foregoing descriptions show the one or more antibodies moveably deposited in detection zone 3, alternate locations for the detector antibodies as well as other reagents are embraced within the present invention. The detector antibody may be provided in the form of, for example, lyophilized beads, such as a single larger bead or multiple smaller beads, placed within the fluid path upstream from the membrane, such that the bead dissolves in the fluid. Non-limiting examples of such beads are described in commonly owned and copending application Ser. No. (Attorney's Docket No. 1112-1-999), incorporated herein by reference. The bead may be provided in a sample delivery channel, the sample circulation channel, or at their junction; a small cavity may be provided in the sample delivery channel or at the junction between the sample delivery channel 18 and the sample circulation channel 19, to hold the material. In another embodiment, the antibody is deposited in lyophilized form within the channel. Other reagents may be so provided, such as reagents to remove interfering substances, as described above. Furthermore, in a device with more than one fluid path in the membrane for carrying out more than one assay, reagents common to the assays may be provided in the fluid path prior to the membrane, and reagents specific to each assay provided in the particular detection zone of the membrane as described above. These various configurations are embraced within the present invention.

As shown in FIGS. 12A and 12B, the sample delivery channel 18 in the bottom surface of the top layer 16 of the device may be designed with a preselected volumetric capacity in order to provide an adequate sample to fill the fluid path of the device and permit the practice of the assay as described above. The sample is applied to the through hole 17 and the sample fills the sample delivery channel starting from the end nearest the through hole 17 and filling towards the opposite end. Once the sample delivery channel is filled, the preselected volume of sample has been applied. A window 91 may be provided, as described below, to indicate that the sample delivery channel has been filled to capacity; the top layer or the portion thereof located above the sample delivery channel may be made of a transparent material such that the filling may be easily observed. Furthermore, and as shown in an example of such a device in FIG. 12A, the sample delivery channel 18 in the top layer 16 may be designed such that once the sample delivery channel 18 has filled with sample to its preselected volume, contact of the moving front of the sample with a narrowed constriction 92 at the opposite end of the channel leading to a narrower capillary channel and to the sample circulation channel 19 will cause the sample in the sample delivery channel to be conducted by capillary action out of the sample delivery channel 18 and into the sample circulation channel 19, then onto the membrane 1, as described above. FIG. 12B shows a cross-section of the device of FIG. 12A along the section marked E—E, showing the sample application through hole 17, the sample delivery channel 18, and the window 91 at the junction between the end of the sample delivery channel 18 and the sample circulation channel 19 to indicate that the sample delivery channel 18 has been filled with adequate sample to conduct the test.

The optional window 91 optionally may be designed as a capillary channel with a flared section at the top surface of the top layer to easily indicate the presence of whole blood at the location. Other arrangements of the window are embraced herein. As mentioned above, an alternate arrangement provides a transparency such that the filling of the sample delivery channel may be observed. In either instance, application of the sample to the through hole may be discontinued when the window indicates that the sample delivery channel is filled, or by direct observation of a full sample delivery channel.

FIG. 13 is a transparent top view of the assembled diagnostic device, and FIGS. 14A–C the top layer 16, membrane 1, and bottom layer 28, respectively. The device illustrated is adapted to diagnose three analytes. The porous carrier is configured with three detection zones 50, 51 and 52 in operative communication with three capture zone channels 27a, 27b and 27c, respectively. For simplicity, this figure does not include the antibodies, red blood cell front, plasma front and other aspects of the novel device. These components are shown in previous figures.

The top layer 16 has a through hole 17 which may be beveled, running from its top surface to the inner surface communicating with the shallow, narrow, sample delivery channel 18, which communicates with the shallow, narrow, sample circulation channel 19 formed in the bottom surface of the top layer 16 with arcuate geometry to conform with the arcuate borders 11 of the detection zones 50, 51 and 52. The circulation channel 19 is closed at both ends 20. Optionally, an extension 53 of an end of the sample circulation channel may be provided with a view window above to serve as an indicator that adequate sample has been applied to the device.

Referring to FIGS. 14A and 14C, top layer 16 is attached to the bottom layer 28 by pins 34 which may be force fit into corresponding holes 35. Any other equivalent means of attachment may be employed and the two layers 16 and 28 may be permanently or removably fixed.

Porous carrier 1 is shown in FIG. 14B with a backing 29 such as a polyester film. It is held between layers 16 and 28 in an optionally recessed area such that the membrane contacts edge 99 of cavity 102. Any such configuration of membrane 1 between top layer 16 and bottom layer 28 is embraced within the present invention so long as there is a operative pathway through which the fluid added by way of through hole 17 can pass through the delivery channel, the circulation channel 19, the detection zones and the capture zone channels to the closed ends of the capture zone channels 27a, 27b, and 27c. The porous membrane 1 shown in FIG. 14B is configured similarly to the porous carrier of FIG. 9 for the detection of three analytes. Accordingly it contains three detection zones 50, 51 and 52, communicating with three capture zone channels 27a, 27b and 27c, respectively. The arcuate border 11 of the detection zones extend over the inner walls 21 of circulation channel 19 so that the flow of fluid when stopped at ends 20 will flow by capillary action into the detection zones 50, 51 and 52.

The purpose of the capillary trap 23 now becomes apparent. If, in the absence of the capillary trap 23, the porous carrier 1 was in contact with a flat bottom surface of the top layer 16, the fluid in the circulation channel 19 would flow between that surface and porous carrier 1 rather than only through the membrane in its preselected pathway from the through hole 17 to the ends of the capture zone channels. The flow is stopped at the ends of the circulation channel to make it possible to control the size of the sample. As mentioned above, an optional window 39 over an optional extension 53 of the sample circulation channel may be provided to indicate that adequate sample has been applied to fill the channel. As noted in FIG. 12A, a window 91 indicating adequate sample volume application may be also provided.

If the top layer 16 is transparent, the formation of a visible reaction product will be readily apparent. If the top layer 16 is opaque it will be constructed with one or more viewing windows, one shown herein as 38, with an optional test window 37. These windows as shown in FIG. 14A will be in registry with the capture zone channels so that the operator can view the formation of colored products or adjust an instrument such as a reflectometer to determine if a detectable reaction product has formed.

The device may have separate windows for viewing the capture zone for each analytes. In preferred devices, there will be one window extending transversely of the top surface 30 so that the results of all of the reactions can be viewed at once. Furthermore, there is an optional window 39 corresponding to an extension of the sample circulation channel below (FIG. 14B), to be used as an indicator that adequate sample has been added to fill the device. The appearance of sample, in particular, blood, under this optional window is an indication that adequate sample has been applied.

One of the advantages of this invention is that the devices whether intended to measure one, two or three antigens can have the same dimensions. Of course, the porous carrier layer 1 will be designed differently in each case. However, the top layer 16 and bottom layer 28 does not require any changes to fit differently designed carrier layers 1.

It will be seen that what has been described is a device and method which permits the detection of components in a liquid sample, for example cardiac analytes in whole blood, serum or plasma, by antigen/antibody reactions utilizing enzyme or direct labels in competitive or sandwich assays. In the devices of the invention, the reactants move along a pathway formed by successive interconnected channels in different planes of the support members and the membrane.

While a variety of nitrocellulose materials are available in various cell sizes, the presently preferred porous carriers are those which, if used as a filter, that is filtering particles from a liquid stream flowing vertically to the horizontal surface of the membrane, will prevent the passage of particles larger than from 3 to 12 $\mu$m. In the practice of the invention, membranes with a pore size from about 5 to 12 $\mu$m, preferably 3 to 8 $\mu$m, are preferred. Some variation is possible. However, as the pore size decreases, the mobility of a fluid within the membrane decreases, thereby increasing the time required for diagnosis. If the pores are too large, the time of passage reduces with the result that the reactants are not in contact with each other for a sufficient period for the diagnostic reactions to occur, or to occur to such a limited extent that they do not provide the desired information.

Nitrocellulose membranes with supporting polyester or other films are commercially available. These are preferred for use in this invention since unsupported membranes tend to be quite fragile, susceptible to fracture and difficult to handle in a mass production environment. Moreover, the films are impervious to the flowing fluids so that they do not interfere with the flow of liquid samples through the chosen pathways of the devices of this invention. One such membrane is available to a variety of pore sizes from Gerbermembrane of Gerbershausen, Germany.

The antibodies employed in this invention are prepared by standard techniques. See for example, Falfre, Howe, Milstein et al., Nature Vol. 266, 7, 550–552, April 1977. The disclosure of this seminal article on the preparation of monoclonal antibodies is incorporated herein by reference.

Procedures for fixing antibodies to substrates such as nitrocellulose are known and usable in producing the devices of this invention. Nitrocellulose is an avid binder for proteins. Hence, the immobile capture antibody need only be applied into the capture zone in a predetermined area. The labelled detector antibody may be movably affixed to the membrane by first saturating the detector zone with another protein such as bovine serum albumin. As noted above, antibodies and other reagents may be deposited in or provided as beads in the fluid bath before the membrane. When the sample used in the assay is whole blood, and separation of red blood cells from the plasma is desired, the reagents provided in the device must not cause lysis of the red blood cells in the sample, to permit the separation.

The device of this invention can be readily manufactured by procedures already well known in the art.

As mentioned above, other assay procedures may be performed using the device of the present invention and its disclosed modifications. This includes both qualitative and quantitative assays, both immunoassay and non-immunoassay formats. Enzyme-based assays, such as the quantitation of glucose in whole blood using the combination of glucose oxidase and peroxidase, with the appropriate reactants and chromogenic substrate to generate a color in proportion to the level of glucose in the sample, may be configured to operate using a device of this invention. The skilled artisan will recognize the adaptability of other assay formats to the present device.

The following non limiting examples are given by way of illustration only.

EXAMPLE 1

Whole Blood CK-MB Test

1A) On a polyester supported cellulose nitrate membrane (3 µm nominal pore size from Gerbermembrane GmbH, Gerbershausen, Germany), a contour as in FIG. 2, is drawn with a Paint Marker 751 yellow (from Edding AG, Ahrensburg, Germany). A capture line is prepared with a 13 mg/ml aqueous streptavidin solution (Streptavidin, poly, from Microcoat GmbH, Benried, Germany). A control line is prepared with a solution containing 80 µl of a 4% (w/v) solution of sucrose (from Sigma-Aldrich GmbH, Steinheim, Germany), 10 µl of water and 10 µl of a 1 mg/ml solution of recombinant CK-MB (from Spectral Diagnostics, Toronto, Canada). After drying, the membrane is impregnated with a blocking solution containing in final concentrations: 0.06% (w/w) Octyl-beta-D-Gluco-pyranoside (from Fluka Chemie AG, Buchs, Switzerland), 1:30 dilution of Kasein-Bindemittel (from H. Schmineke & Co., Erkrath, Germany) and 30 mM 1,4-Piperazinediethanesulfonic acid (from Sigma-Aldrich GmbH, Steinheim, Germany) with a final pH of 6.2. After drying, 2.7 µl of a gold-conjugate solution and 2 µl of a biotinylated antibody solution is applied and the membrane is dried again. The gold-conjugate solution and 2 µl of a biotinylated antibody solution are applied and the membrane is dried again. The gold-conjugate solution is prepared with a 40 nm gold sol loaded with 22 µg/ml of the antibody 5CKMB-6 from Spectral Diagnostics, Toronto, at an OD (520 nm) of 10 prepared by British Biocell International, Cardiff, UK. To 45 µl of this gold-conjugate (OD 10) 45 µl of water and 10 µl of a 2.5% (w/v) aqueous solution of Crotein C (from Croda Chemicals Ltd., UK) is added and mixed. The biotinylated antibody solution is prepared with the antibody 1rCKMB-28 from Spectral Diagnostics, Toronto as described to 57 µl of water 20 µl of a 6% (w/v) aqueous solution of Crotein C and 3 µl of a 2 mg/ml stock solution of the biotinylated antibody solution are added and mixed.

1B) For comparison, tests are prepared as in 1A) but without the biotinylated antibody solution, and instead of the streptavidin capture line an antibody capture line is prepared with the antibody 1rCKMB-28 (from Spectral Diagnostics, Toronto) at a concentration of 13 mg/ml.

Heparinized whole blood is spiked with rCKMB at indicated concentrations and 28 µl are applied to the test. The results (within 6–7 min.) are as follows:

| rCKMB in ng/ml | Streptavidin-Capture | Antibody-Capture |
|---|---|---|
| 0 | – | – |
| 5 | + | n.d. |
| 20 | ++ | n.d. |
| 80 | ++++ | + |

– = no visible signal line
++++ = strong signal line
n.d. = not determined

All control lines are positive.

EXAMPLE 2

Comparison Semicircular to Rectangular CK-MB Test

To demonstrate the versatility of the concept the sample entry in a semicircular area (circle segment) (FIGS. 4 and 5) is compared with a sample entry in a rectangular configuration, i.e. from 3 sides (FIGS. 9 and 10). The test areas (contour areas) are in both cases the same. Beside the contour shape and blood entry directions all other procedures are as in example 1A).

| rCKMB | circle segment | | rectangular | |
|---|---|---|---|---|
| in ng/ml | signal | test time | signal | test time |
| 0 | – | 6.5 min. | – | 7.5 min. |
| 20 | ++ | 7.0 min. | ++ | 7.5 min. |

EXAMPLE 3

Semicircular Area—Three Analytes—One Detection Zone

A test as in example 1B) is prepared, but in addition to the CKMB antibody capture line there is a TNI antibody capture line and a Myoglobin antibody capture line. TNI capture: 13 mg/ml polyclonal goat TNI CKMB capture: 13 mg/ml 1rCKMB-28 Myoglobin capture: 13 mg/ml polyclonal rabbit Myoglobin All antibodies are from Spectral Diagnostics, Toronto. Gold-conjugates for the 3 analytes are from British Biocell Intern., Cardiff, UK: TNI-gold-a: 40 nm gold sol loaded with 8 µg/ml 81-7 antibody (OD 10) TNI-gold-b: 40 nm gold sol loaded with 16 µg/ml 21-14 antibody (OD 10) Myoglobin-gold: 15 nm loaded with 90 µg/ml 2Mb-295 antibody (OD 10) CKMB-gold: 40 nm gold sol loaded with 22 μg/ml 5CKMB-6 (OD 10) All antibodies are from Spectral Diagnostics, Toronto The TNI gold conjugate solution contains: 15 μl of TNI-gold-a at an OD of 33, 30 μl of TNI-gold-b at an OD of 33, 45 μl water and 10 μl of a 2.5% (w/v) aqueous solution of Crotein C. 2.7 μl of this solution is applied to the test area. The CKMB/Myoglobin gold conjugate solution contains: 48 μl of CKMB-gold at an OD of 33, 25 μl of Myoglobin-gold at an OD of 6, 17 μl water and 10 μl of a 2.5% aqueous solution of Crotein C. 2 μl of this solution is applied to the test area.

Heparinized whole blood is spiked with rCKMB, TNI and Myoglobin at indicated concentrations, and 28 μl are applied to the test. The results are as follows:

|  | Signal | | |
| --- | --- | --- | --- |
|  | TNI-capture | CKMB-capture | Myoglobin-capture |
| 0 ng/ml TNI | – | | |
| 0 ng/ml CKMB | | – | |
| 0 ng/ml Myoglobin | | | trace |
| 2 ng/ml TNI | + | | |
| 20 ng/ml CKMB | | + | |
| 200 ng/ml Myoglobin | | | ++ |

Trace: even unspiked blood from a healthy subject can contain trace amounts of myoglobin

EXAMPLE 4

Semicircular Area—Three Analytes—Three Detection Zones

For more than one analyte with high sensitivity a contour as in FIG. 11 is used. The capture lines are prepared with streptavidin (13 mg/ml) as in Example 1A (the blocking procedure likewise). In this example the contour is drawn with Paint Marker 780 white (from Edding AG, Ahrensburg, Germany).

All gold sol-conjugates are prepared by British Biocell International, Cardiff, UK. All antibodies are from Spectral Diagnostics, Toronto. TNI-gold conjugate: The following solutions are mixed: 18 μl gold conjugate A with an OD of 55 (50 nm gold sol loaded with 18 μg/ml of the antibody 81-7 at OD 10), 36 μl gold conjugate B with an OD of 55 (60 nm gold sol loaded with 10 μg/ml of the antibody 21-14 at OD 10), 36 μl water and 10 μl of a 2.5% (w/v) aqueous solution of Crotein C. 1.8 μl is applied to the test area. Biotinylated TNI-antibodies: The following solutions are mixed: 67 μl water, 25 μl of a 6% (w/v) aqueous solution of Crotein C, 3.5 μl of a 1 mg/ml stock solution of biotinylated goat TNI antibodies and 5 μl of a 27.6 mg/ml solution of Chrom Pure Goat IgG (from Jackson Immuno Research Laboratories Inc.). 2.1 μl of this solution is applied to the test area.

CKMB-gold conjugate: As in example 1A), except that the OD of the stock solution is 33, and 1.1 μl of the mixture is applied. Biotinylated CKMB-antibodies: As in example 1A), except that 1.4 μl is applied. Myoglobin-gold conjugate: The following solutions are mixed: 17 μl of a gold conjugate with an OD of 6 (15 nm gold sol loaded with 90 μg/ml of the antibody 2Mb-295 at OD 10), 73 μl water and 10 μl of a 2.5% (w/v) aqueous solution of Crotein C. 0.8 μl of this mixture is applied to the test. Biotinylated Myoglobin-antibodies: The following solutions are mixed: 45 μl water, 25 μl of a 6% (w/v) aqueous solution of Crotein C and 30 μl of a 1 mg/ml stock solution of biotinylated rabbit antibodies Myoglobin. 0.5 μl of this mixture is applied to the test.

Heparinized whole blood is spiked with rCKMB, TNI and Myoglobin at indicated concentrations, and 70 μl is applied to the test. The results (within 10 to 12 min.) are as follows:

|  | Signal | | |
| --- | --- | --- | --- |
|  | TNI | CKMB | Myoglobin |
| 0 ng/ml TNI | – | | |
| 0 ng/ml CKMB | | – | |
| 0 ng/ml Myoglobin | | | – |
| 2 ng/ml TNI | ++ | | |
| 20 ng/ml CKMB | | ++ | |
| 200 ng/ml Myoglobin | | | ++ |
| 10 ng/ml TNI | ++++ | | |
| 100 ng/ml CKMB | | ++++ | |
| 700 ng/ml Myoglobin | | | ++++ |

It is to be understood that the invention is not limited to the illustrations described and shown herein which are deemed to be merely illustrative of the best modes of carrying out the invention and which are susceptible of modifications of form, size, arrangement of parts and details of operation without departing from the spirit or scope of the invention. The invention, rather, is intended to encompass all such modifications which are within the spirit and scope of the claims.

What is claimed is:

1. An analytical test device suitable for determining the presence of at least one analyte contained in a sample while permitting rapid and efficient flow of the sample through at least one defined pathway in which reactions determinative of the analyte take place, said device comprising:

a top layer having an upper surface formed with a through hole for the addition of the sample, said through hole being in registry with a sample delivery channel formed in a lower surface of the top layer, said sample delivery channel having walls defined by said lower surface of said top layer and an upper surface of a bottom layer, said sample delivery channel in operative communication with a sample circulation channel closed at its terminal ends and formed with inner and outer walls to define a pathway for the sample in the lower surface of the top layer, the inner walls of the circulation channel defining an indent in the lower surface of the top layer;

the bottom layer attached to the top layer, a dry porous carrier therebetween in contact with said walls of said sample circulation channel and providing a fluid pathway therefrom;

said fluid pathway of said dry porous carrier layer configured to contain at least one detection zone having a border in operative communication with the sample circulation channel, the sample being permitted to enter into said detection zone from said sample circulation channel from a plurality of different directions; and an opposite end in operative communication with a capture zone channel having an entrance end and a closed terminal end to provide a conduit through which the liquid sample may flow by capillary action from the sample circulation channel to the terminal end of the capture zone channel, the distances between all points where the sample is permitted to enter the detection zone and said entrance end being essentially the same;

the sample delivery channel, sample circulation channel, detection zone and capture zone channel forming a defined pathway through which the liquid sample flows from the through hole to the terminal end of the capture channel;

there being immobilized reagent in the capture zone channel which will react with said analyte to form a detectable product.

2. The device of claim 1 in which the sample circulation channel is arcuate.

3. The device of claim 1 in which the liquid sample is selected from the group consisting of whole blood, plasma, serum and urine.

4. The device of claim 1 wherein the analyte is selected from the group consisting of myoglobin, CK-MB, either troponin I or troponin T, and combinations thereof.

5. The device of claim 1 wherein the analyte is selected from the group consisting of human chorionic gonadotropin, luteinizing hormone and the combination thereof.

6. The device of claim 1 wherein the top layer is transparent and the detectable reaction product is visible.

7. The device of claim 1 wherein the top layer is opaque and has a view window or transparency through which the detectable reaction product is visible.

8. The device of claim 1 wherein a mobile labeled reagent is provided, said reagent is a labelled antibody which will react with one epitope on the analyte and the immobilized reagent is an antibody which will react with another epitope on the analyte.

9. The device of claim 8 comprising a mixture of a mobile labelled antibody which will react with one epitope on the analyte and a mobile biotin labelled antibody which will react with another epitope on the analyte, and the immobilized reagent is an avidin.

10. The device of claim 9 wherein the immobilized reagent is selected from the group consisting of streptavidin and avidin.

11. The device of claim 8 wherein a label on said mobile labeled reagent is a direct particulate label.

12. The device of claim 11 wherein the label is a gold label.

13. The device of claim 8 wherein said mobile reagent is provided in the detection zone.

14. The device of claim 8 wherein said mobile reagent is provided in the fluid path prior to the membrane.

15. The device of claim 1 in which the dry porous carrier is nitrocellulose.

16. The device of claim 1 containing two pathways, one containing the reagents for determining the presence of myoglobin, the other containing the reagents for determining the presence of CK-MB.

17. The device of claim 1 containing three pathways, the one pathway containing the reagents for determining the presence of troponin I or troponin T, another pathway containing the reagents for determining the presence of myoglobin and still another pathway containing the reagents for determining the presence of CK-MB.

18. The device of claim 1 containing the reagents for determining the presence of troponin I.

19. The device of claim 1 in which there is only one pathway and it contains the reagents for determining the presence of myoglobin and CK-MB.

20. The device of claim 1 in which there is only one pathway and it contains the reagents for determining the presence of troponin I or troponin T together with the reagents for determining the presence of myoglobin and CK-MB.

21. The device of claim 1 wherein a window is provided at a junction between said sample delivery channel and said sample circulation channel to indicate that sufficient sample has been added to said sample delivery channel to conduct said determining of at said at least one analyte.

22. The device of claim 1 wherein said sample delivery channel has a predetermined capacity corresponding to a volume of sample needed to conduct said determining of said at least one analyte, said sample delivery channel having means for conducting said predetermined volume of sample from said sample delivery channel to said sample circulation channel when said sample delivery channel is filled with said predetermined volume.

23. The device of claim 22 wherein the portion of said sample delivery channel in operative communication with said sample circulation channel comprises a narrowed capillary portion leading to said sample circulation channel, wherein when the sample delivery channel is filled with said sample to the point of contact with said narrowed capillary portion, said sample is conducted to the sample circulation channel.

24. The device of claim 1 wherein said border of said detection zone is semicircular.

25. The device of claim 1 wherein said sample circulation channel is polygonal or forms part of a polygon.

26. The device of claim 25 wherein said sample circulation channel is rectangular or forms part of a rectangle.

27. The device of claim 1 wherein said border of said detection zone is polygonal or forms part of a polygon.

28. The device of claim 27 wherein said border of said detection zone is rectangular or forms part of a rectangle.

29. A method for determining the presence of at least one analyte contained in a liquid sample while permitting rapid and efficient flow of the sample through at least one defined pathway in which reactions determinative of the analyte take place, said method comprising:

i) providing a top layer having an upper surface formed with a through hole for the addition of the sample, said through hole being in registry with a sample delivery channel formed in a lower surface of the top layer, said sample delivery channel having walls defined by said lower surface of said top layer and an upper surface of a bottom layer, said sample delivery channel in operative communication with a sample circulation channel closed at its terminal ends and formed with inner and outer walls to define a pathway for the sample in the lower surface of the top layer, the inner walls of the circulation channel defining an indent in the lower surface of the top layer;

ii) providing the bottom layer attached to the top layer, a dry porous carrier therebetween in contact with said walls of said sample circulation channel and providing a fluid pathway therefrom, said fluid pathway of said dry porous carrier layer configured to contain at least one detection zone having a border in operative communication with the sample circulation channel, the sample being permitted to enter into said detection zone from said sample circulation channel from a plurality of different directions; and an opposite end in operative communication with a capture zone channel having an entrance end and a closed terminal end to provide a conduit through which the liquid sample may flow by capillary action from the sample circulation channel to the terminal end of the capture zone channel; the sample delivery channel, sample circulation channel, detection zone and capture zone channel forming a defined pathway through which the liquid sample flows from the through hole to the terminal end of the capture channel; there being immobilized reagent in the capture zone channel which will react with said analyte to form a detectable product;

iii) applying a quantity of said fluid sample to said detection zone;

iv) permitting a sufficient period of time to elapse for the fluid sample to flow from the detection zone from said plurality of different directions to the capture zone channel and any said analyte therein to form a detectable reaction product at said capture zone; and v) identifying the presence of said at least one analyte in said fluid sample by detecting any said detectable reaction product at said capture zone.

30. The method of claim 29 wherein said at least one analyte is a cardiac analyte.

31. The method of claim 29 wherein three pathways are provided for identifying the presence of troponin I or troponin T together with identifying the presence of myoglobin and CK-MB.

32. The method of claim 29 wherein there is only one pathway provided for identifying the presence of troponin I or troponin T together with the identifying the presence of myoglobin and CK-MB.

33. The method of claim 29 wherein distances between all points where the sample is permitted to enter the detection zone and said entrance end are essentially the same.

34. The method of claim 29 wherein said sample circulation channel is arcuate.

35. The method of claim 29 wherein said border of said detection zone is semicircular.

36. The method of claim 29 wherein said sample circulation channel is polygonal or forms part of a polygon.

37. The method of claim 36 wherein said sample circulation channel is rectangular or forms part of a rectangle.

38. The method of claim 29 wherein said border of said detection zone is polygonal or forms part of a polygon.

39. The method of claim 38 wherein said border of said detection zone is rectangular or forms part of a rectangle.

40. An analytical test device suitable for determining the presence of at least one analyte contained in a liquid sample while permitting rapid and efficient flow of the sample through at least one defined pathway in which reactions determinative of the analyte take place, said device comprising:

a top layer having an upper surface formed with a through hole for the addition of the sample, said through hole being in registry with a sample delivery channel formed in a lower surface of the top layer, said sample delivery channel having walls defined by said lower surface of said top layer and an upper surface of a bottom layer, said sample delivery channel in operative communication with a sample circulation channel closed at its terminal ends and formed with inner and outer walls to define a pathway for the sample in the lower surface of the top layer, the inner walls of the circulation channel defining an indent in the lower surface of the top layer;

the bottom layer attached to a top layer, said dry porous carrier therebetween in contact with said walls of said sample circulation channel and providing a fluid pathway therefrom;

said fluid pathway of said dry porous carrier layer configured to contain at least one detection zone having a border in operative communication with the sample circulation channel, the sample being permitted to enter into said detection zone from said sample circulation channel from a plurality of different directions; and an opposite end in operative communication with a capture zone channel having an entrance end and a closed terminal end to provide a conduit through which the liquid sample may flow by capillary action from the sample circulation channel to the terminal end of the capture zone channel;

the sample delivery channel, sample circulation channel, detection zone and capture zone channel forming a defined pathway through which the liquid sample flows from the through hole to the terminal end of the capture channel;

there being immobilized reagent in the capture zone channel which will react with said analyte to form a detectable product.

41. The device of claim 40 wherein said sample circulation channel is polygonal or forms part of a polygon.

42. The device of claim 41 wherein said sample circulation channel is rectangular or forms part of a rectangle.

43. The device of claim 40 wherein said border of said detection zone is polygonal or forms part of a polygon.

44. The device of claim 43 wherein said border of said detection zone is rectangular or forms part of a rectangle.

45. The device of claim 40 further comprising at least one mobile, labelled reagent which will specifically react with the analyte to form a labelled complex which will move by capillary action into the capture zone channel; and there being immobilized reagent in the capture zone channel which will react with and concentrate the labelled complex to form a detectable reaction product.

46. The device of claim 45 wherein the mobile, labelled reagent is provided in the detection zone, said mobile reagent being a labelled antibody which will react with one epitope on the analyte and the immobilized reagent is an antibody which will react with another epitope on the analyte.

47. The device of claim 45 wherein a label on said mobile, labelled reagent is a particulate direct label.

48. The device of claim 47 wherein the label is a gold label.

49. The device of claim 40 in which the liquid sample is selected from the group consisting of whole blood, plasma, serum and urine.

50. The device of claim 40 wherein the analyte is selected from the group consisting of myoglobin, CK-MB either troponin I or troponin T, and combinations thereof.

51. The device of claim 40 wherein the analyte is selected from the group consisting of human chorionic gonadotropin, luteinizing hormone and mixtures thereof.

52. The device of claim 40 comprising a mixture of a mobile labelled antibody which will react with one epitope on the analyte and a mobile biotin labelled antibody which will react with another epitope on the analyte, and the immobilized reagent is an avidin.

53. The device of claim 52 wherein, the immobilized reagent is selected from the group consisting of streptavidin and avidin.

54. The device of claim 40 in which the dry porous carrier is nitrocellulose.

55. The device of claim 40 containing the reagents for determining the presence of troponin I or troponin T.

56. The device of claim 40 containing two pathways, one containing the reagents for determining the presence of myoglobin, the other containing the reagents for determining the presence of CK-MB.

57. The device of claim 40 containing three pathways, the one pathway containing the reagents for determining the presence of troponin I or troponin T, another pathway containing the reagents for determining the presence of myoglobin and still another pathway containing the reagents for determining the presence of CK-MB.

58. The device of claim 40 in which contains only the reagents for determining the presence of troponin I.

59. The device of claim 40 in which there is only one pathway and it contains the reagents for determining the presence of myoglobin and CK-MB.

60. The device of claim 40 in which there is only one pathway and it contains the reagents for determining the presence of troponin I or troponin T together with the reagents for determining the presence of myoglobin and CK-MB.

61. The device of claim 40 wherein said sample delivery channel has a predetermined capacity corresponding to a volume of sample needed to conduct said determining of said at least one analyte, said sample delivery channel having means for conducting said predetermined volume of sample from said sample delivery channel to said sample circulation channel when said sample delivery channel is filled with said predetermined volume.

62. The device of claim 61 wherein the portion of said sample delivery channel in operative communication with said sample circulation channel comprises a narrowed capillary portion leading to said sample circulation channel, wherein when the sample delivery channel is filled with said sample to the point of contact with said narrowed capillary portion, said sample is conducted to the sample circulation channel.

63. The device of claim 40 wherein a dried reagent is present in said sample delivery channel.

64. The device of claim 63 wherein said dried reagent is selected from the group consisting of a labeled antibody to said analyte, a biotinylated antibody to said analyte, and the combination thereof.

* * * * *